(12) United States Patent
Deutch

(10) Patent No.: US 11,413,026 B2
(45) Date of Patent: Aug. 16, 2022

(54) MAGNARETRACTOR SYSTEM AND METHOD

(71) Applicant: Attractive Surgical, LLC, Highland Park, IL (US)

(72) Inventor: Todd Deutch, Highland Park, IL (US)

(73) Assignee: ATTRACTIVE SURGICAL, LLC, Highland Park, IL (US)

( * ) Notice: Subject to any disclaimer, the term of this patent is extended or adjusted under 35 U.S.C. 154(b) by 141 days.

(21) Appl. No.: 16/528,878

(22) Filed: Aug. 1, 2019

(65) Prior Publication Data

US 2019/0350575 A1 Nov. 21, 2019

Related U.S. Application Data

(63) Continuation of application No. 16/419,363, filed on May 22, 2019, which is a continuation of application
(Continued)

(51) Int. Cl.
*A61B 17/02* (2006.01)
*A61B 34/00* (2016.01)
(Continued)

(52) U.S. Cl.
CPC .......... *A61B 17/0218* (2013.01); *A61B 34/70* (2016.02); *A61B 34/73* (2016.02); *A61B 90/14* (2016.02); *A61D 1/16* (2013.01); *A61N 2/002* (2013.01); *A61N 2/02* (2013.01); *A61B 17/0281* (2013.01); *A61B 17/0682* (2013.01);
(Continued)

(58) Field of Classification Search
CPC ........ A61B 2019/0234; A61B 19/0256; A61B 19/0257; A61B 2017/12086; A61B 17/0218; A61B 1/00158; A61B 5/062
See application file for complete search history.

(56) References Cited

U.S. PATENT DOCUMENTS 2,678,228 A 5/1954 Gerhardt
2,863,444 A 12/1958 Winsten
(Continued)

FOREIGN PATENT DOCUMENTS

CA 2748471 7/2010
CA 2733465 9/2011
(Continued)

OTHER PUBLICATIONS

Patent Trial and Appeal Board, IPR2019-01294, U.S. Pat. No. 9,386,973, Decision Granting Institution of Inter Partes Review, Jan. 22, 2020.
(Continued)

*Primary Examiner* — Anu Ramana
(74) *Attorney, Agent, or Firm* — Cooley LLP

(57) ABSTRACT

A system and method for performing surgical procedures within a body cavity, e.g. abdomen, uses a magnetized device is utilized to allow a surgeon to control intra-abdominal organs and objects. The system and method allows a surgeon to perform an intra-abdominal procedure without the need to position surgical tools inside of the body cavity. Additional surgical ports are not necessary as the magnetized device allows the surgeon to retract or position various objects within the abdomen.

6 Claims, 20 Drawing Sheets

Related U.S. Application Data

No. 15/966,958, filed on Apr. 30, 2018, now Pat. No. 10,335,134, which is a continuation of application No. 14/918,974, filed on Oct. 21, 2015, now Pat. No. 9,962,148, which is a continuation of application No. 14/074,783, filed on Nov. 8, 2013, now Pat. No. 9,386,973, which is a continuation of application No. 12/787,998, filed on May 26, 2010, now Pat. No. 8,602,981, which is a continuation-in-part of application No. PCT/US2008/084991, filed on Nov. 26, 2008.

(60) Provisional application No. 60/996,575, filed on Nov. 26, 2007.

(51) Int. Cl.
| | |
|---|---|
| *A61B 90/14* | (2016.01) |
| *A61N 2/00* | (2006.01) |
| *A61N 2/02* | (2006.01) |
| *A61D 1/16* | (2006.01) |
| A61B 17/068 | (2006.01) |
| A61B 17/42 | (2006.01) |
| A61B 17/00 | (2006.01) |
| A61B 17/04 | (2006.01) |
| A61B 17/064 | (2006.01) |
| A61B 17/29 | (2006.01) |
| A61B 46/10 | (2016.01) |

(52) U.S. Cl.
CPC ........... *A61B 17/4241* (2013.01); *A61B 46/10* (2016.02); *A61B 2017/00398* (2013.01); *A61B 2017/00464* (2013.01); *A61B 2017/00818* (2013.01); *A61B 2017/00876* (2013.01); *A61B 2017/0409* (2013.01); *A61B 2017/0649* (2013.01); *A61B 2017/2931* (2013.01); *A61B 2017/2932* (2013.01); *A61B 2034/733* (2016.02)

(56) References Cited

U.S. PATENT DOCUMENTS

| | | |
|---|---|---|
| 3,146,381 A | 8/1964 | Louis |
| 3,674,014 A | 7/1972 | Tillander |
| 3,789,285 A | 1/1974 | Nishizawa |
| 3,794,091 A | 2/1974 | Ersek et al. |
| 4,364,377 A | 12/1982 | Smith |
| 4,380,999 A | 4/1983 | Healy |
| 4,706,668 A | 11/1987 | Backer et al. |
| 4,756,312 A | 7/1988 | Epley |
| 4,901,405 A | 2/1990 | Grover et al. |
| 4,915,435 A | 4/1990 | Levine |
| 4,968,136 A | 11/1990 | Lim et al. |
| 4,971,067 A | 11/1990 | Bolduc et al. |
| 4,976,723 A | 12/1990 | Schad |
| 4,997,436 A | 3/1991 | Oberlander |
| 5,002,557 A | 3/1991 | Hasson |
| 5,154,189 A | 10/1992 | Oberlander |
| 5,156,608 A | 10/1992 | Troidl et al. |
| 5,156,609 A | 10/1992 | Nakao et al. |
| 5,282,806 A | 2/1994 | Haber et al. |
| 5,300,081 A | 4/1994 | Young et al. |
| 5,304,183 A | 4/1994 | Gourlay et al. |
| 5,304,185 A | 4/1994 | Taylor |
| 5,307,805 A | 5/1994 | Byrne |
| 5,340,360 A | 8/1994 | Stefanchik |
| 5,397,325 A | 3/1995 | Della Badia et al. |
| 5,411,535 A | 5/1995 | Fujii et al. |
| 5,415,160 A | 5/1995 | Ortiz et al. |
| 5,417,701 A | 5/1995 | Holmes |
| 5,449,361 A | 9/1995 | Preissman |
| 5,449,365 A | 9/1995 | Green et al. |
| 5,450,842 A | 9/1995 | Tovey |
| 5,458,603 A | 10/1995 | Futch, Sr. |
| 5,458,693 A | 10/1995 | Codorniu |
| 5,465,711 A | 11/1995 | Moll et al. |
| 5,496,317 A | 3/1996 | Goble et al. |
| 5,499,986 A | 3/1996 | Dimarco |
| 5,529,568 A | 6/1996 | Rayman |
| 5,538,098 A | 7/1996 | Sparhawk |
| 5,564,864 A | 10/1996 | Ritter et al. |
| 5,593,379 A | 1/1997 | Rayman |
| 5,595,562 A | 1/1997 | Grier et al. |
| 5,665,100 A | 9/1997 | Yoon |
| 5,681,260 A | 10/1997 | Ueda et al. |
| 5,728,121 A | 3/1998 | Bimbo et al. |
| 5,733,292 A | 3/1998 | Gustilo et al. |
| 5,749,881 A | 5/1998 | Sackier et al. |
| 5,766,189 A | 6/1998 | Matsuno |
| 5,782,748 A | 7/1998 | Palmer et al. |
| 5,797,911 A | 8/1998 | Sherman et al. |
| 5,797,939 A | 8/1998 | Yoon |
| 5,848,969 A | 12/1998 | Panescu et al. |
| 5,849,015 A | 12/1998 | Haywood et al. |
| 5,888,196 A | 3/1999 | Bonutti |
| 5,893,873 A | 4/1999 | Rader |
| 5,933,926 A | 8/1999 | Reiter |
| 6,015,414 A | 1/2000 | Werp |
| 6,017,358 A | 1/2000 | Yoon et al. |
| 6,096,038 A | 8/2000 | Michelson |
| 6,099,537 A | 8/2000 | Sugai |
| 6,099,550 A | 8/2000 | Yoon |
| 6,123,657 A | 9/2000 | Ishikawa et al. |
| 6,126,657 A | 10/2000 | Posey et al. |
| 6,127,757 A | 10/2000 | Swinbanks |
| 6,165,180 A | 12/2000 | Cigaina et al. |
| 6,173,715 B1 | 1/2001 | Sinanan et al. |
| 6,212,419 B1 | 4/2001 | Blume et al. |
| 6,216,028 B1 | 4/2001 | Haynor et al. |
| 6,241,671 B1 | 6/2001 | Ritter et al. |
| 6,311,082 B1 | 10/2001 | Creighton, IV et al. |
| 6,315,709 B1 | 11/2001 | Gaibaldi et al. |
| 6,330,467 B1 | 12/2001 | Creighton, IV et al. |
| 6,358,196 B1 | 3/2002 | Rayman |
| 6,371,973 B1 | 4/2002 | Tepper |
| 6,398,791 B1 | 6/2002 | Que et al. |
| 6,399,146 B1 | 6/2002 | Harris et al. |
| 6,401,723 B1 | 6/2002 | Garibaldi et al. |
| 6,440,133 B1 | 8/2002 | Beale et al. |
| 6,458,146 B1 | 10/2002 | Kramer |
| 6,459,924 B1 | 10/2002 | Creighton, IV et al. |
| 6,464,710 B1 | 10/2002 | Foster |
| 6,340,365 B2 | 11/2002 | Dittrich |
| 6,488,615 B1 | 12/2002 | Mitchiner et al. |
| 6,523,919 B1 | 2/2003 | Israelsen et al. |
| 6,537,196 B1 | 3/2003 | Creighton, IV et al. |
| 6,551,304 B1 | 4/2003 | Whalen et al. |
| 6,594,517 B1 | 7/2003 | Nevo |
| 6,630,879 B1 | 10/2003 | Creighton, IV et al. |
| 6,632,229 B1 | 10/2003 | Yamanouchi |
| 6,641,595 B1 | 11/2003 | Moran et al. |
| 6,656,199 B1 | 12/2003 | Lafontaine |
| 6,677,752 B1 | 1/2004 | Creighton, IV et al. |
| 6,689,119 B1 | 2/2004 | Di Caprio et al. |
| 6,702,804 B1 | 3/2004 | Ritter et al. |
| 6,705,989 B2 | 3/2004 | Cuschieri et al. |
| 6,719,765 B2 | 4/2004 | Bonutti |
| 6,761,861 B2 | 7/2004 | Schmid et al. |
| 6,786,219 B2 | 9/2004 | Garibaldi et al. |
| 6,817,364 B2 | 11/2004 | Garibaldi et al. |
| 6,824,511 B1 | 11/2004 | Bell et al. |
| 6,916,314 B2 | 7/2005 | Schneider et al. |
| 7,017,584 B2 | 3/2006 | Garibaldi et al. |
| 7,094,245 B2 | 8/2006 | Adams et al. |
| 7,169,104 B2 | 1/2007 | Ueda et al. |
| 7,182,089 B2 | 2/2007 | Ries |
| 7,182,775 B2 | 2/2007 | De Guillebon et al. |
| 7,189,198 B2 | 3/2007 | Harburn et al. |
| 7,264,584 B2 | 9/2007 | Ritter et al. |
| 7,300,400 B2 | 11/2007 | Brown |
| 7,311,107 B2 | 12/2007 | Harel et al. |

(56) References Cited

U.S. PATENT DOCUMENTS

| | | |
|---|---|---|
| 7,313,429 B2 | 12/2007 | Creighton, IV et al. |
| 7,314,063 B2 | 1/2008 | Egli |
| 7,341,063 B2 | 3/2008 | Garbibaldi et al. |
| 7,344,553 B2 | 3/2008 | Opolski et al. |
| 7,390,298 B2 | 6/2008 | Chu |
| 7,416,335 B2 | 8/2008 | Munger |
| 7,429,259 B2 | 9/2008 | Cadeddu et al. |
| 7,431,726 B2 | 10/2008 | Spence et al. |
| 7,566,038 B2 | 7/2009 | Scott et al. |
| 7,618,435 B2 | 11/2009 | Opolski |
| 7,686,827 B2 | 3/2010 | Hushka |
| 7,691,103 B2 | 4/2010 | Fernandez et al. |
| 7,691,731 B2 | 4/2010 | Bet et al. |
| 7,693,903 B2 | 4/2010 | Ghiron et al. |
| 7,708,756 B2 | 5/2010 | Nobis et al. |
| 7,736,356 B2 | 6/2010 | Cooper et al. |
| 7,766,810 B2 | 8/2010 | Ohdaira |
| 7,769,427 B2 | 8/2010 | Shachar |
| 7,772,950 B2 | 8/2010 | Tunay |
| 7,774,046 B2 | 8/2010 | Werp et al. |
| 7,780,054 B2 | 8/2010 | Wales |
| 7,799,050 B2 | 9/2010 | Hensley et al. |
| 7,837,612 B2 | 11/2010 | Gill et al. |
| 7,850,591 B2 | 12/2010 | Spector |
| 7,942,885 B2 | 5/2011 | Sixto, Jr. et al. |
| 7,966,059 B2 | 6/2011 | Creighton, IV et al. |
| 7,967,830 B2 | 6/2011 | Ayala et al. |
| 8,038,612 B2 | 10/2011 | Paz |
| 8,043,290 B2 | 10/2011 | Harrison et al. |
| 8,057,472 B2 | 11/2011 | Walker et al. |
| 8,060,184 B2 | 11/2011 | Hastings et al. |
| 8,066,715 B2 | 11/2011 | Ducharme |
| 8,074,657 B2 | 12/2011 | Scott et al. |
| 8,082,035 B2 | 12/2011 | Glukhovsky |
| 8,133,254 B2 | 3/2012 | Dumbauld et al. |
| 8,136,888 B2 | 3/2012 | Suzuki |
| 8,137,268 B2 | 3/2012 | Van Lue |
| 8,157,149 B2 | 4/2012 | Olson et al. |
| 8,187,286 B2 | 5/2012 | Jugenheimer et al. |
| 8,197,494 B2 | 6/2012 | Jaggi et al. |
| 8,226,690 B2 | 7/2012 | Altarac et al. |
| 8,235,272 B2 | 8/2012 | Nicholas et al. |
| 8,241,322 B2 | 8/2012 | Whitman et al. |
| 8,246,529 B2 | 8/2012 | Riehl et al. |
| 8,252,021 B2 | 8/2012 | Boulnois et al. |
| 8,267,854 B2 | 9/2012 | Asada et al. |
| 8,301,226 B2 | 10/2012 | Csavoy et al. |
| 8,303,495 B2 | 11/2012 | Ducharme |
| 8,313,497 B2 | 11/2012 | Walberg et al. |
| 8,316,861 B2 | 11/2012 | Brewer et al. |
| 8,316,862 B2 | 11/2012 | Shapiro et al. |
| 8,333,695 B2 | 12/2012 | Cuschieri |
| 8,343,171 B2 | 1/2013 | Farritor |
| 8,360,972 B2 | 1/2013 | Paz |
| 8,364,277 B2 | 1/2013 | Glukhovsky |
| 8,377,044 B2 | 2/2013 | Coe et al. |
| 8,382,754 B2 | 2/2013 | Odom et al. |
| 8,403,916 B2 | 3/2013 | Prescott |
| 8,480,668 B2 | 7/2013 | Fernandez et al. |
| 8,491,626 B2 | 7/2013 | Roy et al. |
| 8,517,931 B2 | 8/2013 | Minnelli et al. |
| 8,518,057 B2 | 8/2013 | Walberg |
| 8,556,919 B2 | 10/2013 | Aquirre et al. |
| 8,579,787 B2 | 11/2013 | Shapiro et al. |
| 8,585,685 B2 | 11/2013 | Hagg |
| 8,602,981 B2 | 12/2013 | Deutch |
| 8,608,773 B2 | 12/2013 | Tierny et al. |
| 8,623,011 B2 | 1/2014 | Spivey |
| 8,628,529 B2 | 1/2014 | Aldridge et al. |
| 8,636,762 B2 | 1/2014 | Whitman et al. |
| 8,637,818 B2 | 1/2014 | Balakin |
| 8,685,043 B2 | 4/2014 | Jugenheimer et al. |
| 8,758,394 B2 | 6/2014 | Zimmerling et al. |
| 8,764,769 B1 | 7/2014 | Rodriguez Navarro et al. |
| 8,790,245 B2 | 7/2014 | Rodriguez Fernandez et al. |
| 8,820,602 B2 | 9/2014 | Walberg |
| 8,827,891 B2 | 9/2014 | Roberts |
| 8,828,024 B2 | 9/2014 | Farritor |
| 8,894,574 B2 | 11/2014 | Ellman |
| 8,926,656 B2 | 1/2015 | Palermo et al. |
| 8,944,997 B2 | 2/2015 | Fernandez et al. |
| 8,968,332 B2 | 3/2015 | Farritor et al. |
| 8,968,356 B2 | 3/2015 | Mueller |
| 9,011,468 B2 | 4/2015 | Ketai et al. |
| 9,033,957 B2 | 5/2015 | Cadeddu et al. |
| 9,044,256 B2 | 6/2015 | Cadeddu et al. |
| 9,339,285 B2 | 5/2016 | Rodriguez-Navarro et al. |
| 9,386,973 B2 | 7/2016 | Deutch |
| 9,561,031 B2 | 2/2017 | Heinrich et al. |
| 9,627,120 B2 | 4/2017 | Scott et al. |
| 9,844,391 B2 | 12/2017 | Rodriguez Fernandez et al. |
| 9,962,148 B2 | 5/2018 | Deutch |
| 9,974,546 B2 | 5/2018 | Rodriguez Fernandez et al. |
| 10,010,370 B2 | 7/2018 | Rodriguez-Navarro et al. |
| 10,130,381 B2 | 11/2018 | Rodriguez-Navarro et al. |
| 10,143,459 B2 | 12/2018 | Heftman |
| 10,335,134 B2 | 7/2019 | Deutch |
| 10,537,348 B2 | 1/2020 | Rodriguez-Navarro et al. |
| 10,905,511 B2 | 2/2021 | Rodriguez-Navarro et al. |
| 11,020,137 B2 | 6/2021 | Rodriguez-Navarro |
| 2001/0038683 A1 | 11/2001 | Ritter et al. |
| 2002/0100486 A1 | 8/2002 | Creighton, IV et al. |
| 2002/0107533 A1 | 8/2002 | Solingen |
| 2002/0116043 A1 | 8/2002 | Garibaldi et al. |
| 2002/0173805 A1 | 11/2002 | Matsuno et al. |
| 2003/0114731 A1 | 6/2003 | Cadeddu et al. |
| 2003/0125752 A1 | 7/2003 | Werp et al. |
| 2003/0181945 A1 | 9/2003 | Opolski |
| 2003/0208185 A1 | 11/2003 | Sheffer et al. |
| 2004/0044295 A1 | 3/2004 | Reinert et al. |
| 2004/0050395 A1 | 3/2004 | Ueda et al. |
| 2004/0064153 A1 | 4/2004 | Creighton et al. |
| 2004/0068173 A1 | 4/2004 | Viswanathan |
| 2004/0158972 A1 | 8/2004 | Creighton, IV et al. |
| 2004/0172057 A1 | 9/2004 | Guillebon et al. |
| 2004/0176797 A1 | 9/2004 | Opolski |
| 2004/0186347 A1 | 9/2004 | Shose et al. |
| 2004/0199074 A1 | 10/2004 | Ritter et al. |
| 2004/0230100 A1 | 11/2004 | Shluzas |
| 2004/0249262 A1 | 12/2004 | Werp et al. |
| 2005/0080440 A1 | 4/2005 | Durgin et al. |
| 2005/0085696 A1 | 4/2005 | Uchiyama et al. |
| 2005/0113628 A1 | 5/2005 | Creighton, IV et al. |
| 2005/0131390 A1 | 6/2005 | Heinrich et al. |
| 2005/0165449 A1 | 7/2005 | Cadeddu et al. |
| 2005/0220583 A1 | 10/2005 | Lutz |
| 2005/0250988 A1 | 11/2005 | Ewers et al. |
| 2005/0277975 A1 | 12/2005 | Saadat et al. |
| 2006/0015178 A1 | 1/2006 | Moaddeb et al. |
| 2006/0074448 A1 | 4/2006 | Harrison et al. |
| 2006/0079897 A1 | 4/2006 | Harrison et al. |
| 2006/0089633 A1 | 4/2006 | Bleich et al. |
| 2006/0116714 A1 | 6/2006 | Sepetka et al. |
| 2006/0149135 A1 | 7/2006 | Paz |
| 2006/0152309 A1 | 7/2006 | Mintchev |
| 2006/0228421 A1 | 10/2006 | Seeney et al. |
| 2006/0241691 A1 | 10/2006 | Wilk |
| 2006/0247522 A1 | 11/2006 | Megee |
| 2006/0276738 A1 | 12/2006 | Becker |
| 2006/0293566 A1 | 12/2006 | Brown |
| 2007/0004958 A1 | 1/2007 | Ohdaira |
| 2007/0016010 A1 | 1/2007 | Creighton, IV et al. |
| 2007/0027458 A1 | 2/2007 | Sixto et al. |
| 2007/0043359 A1 | 2/2007 | Altarac et al. |
| 2007/0073102 A1 | 3/2007 | Matsuno et al. |
| 2007/0135678 A1* | 6/2007 | Suzuki ............... A61B 17/1227 600/37 |
| 2007/0135685 A1 | 6/2007 | Cuschieri |
| 2007/0135802 A1 | 6/2007 | Suzuki |
| 2007/0135803 A1 | 6/2007 | Belson |
| 2007/0156028 A1 | 7/2007 | Van Lue et al. |
| 2007/0191670 A1 | 8/2007 | Spector |
| 2007/0221233 A1 | 9/2007 | Kawano et al. |
| 2007/0255273 A1 | 11/2007 | Fernandez et al. |

(56) References Cited

U.S. PATENT DOCUMENTS

| | | |
|---|---|---|
| 2007/0270629 A1 | 11/2007 | Charles |
| 2007/0282311 A1 | 12/2007 | Scott et al. |
| 2008/0081883 A1 | 4/2008 | King, II et al. |
| 2008/0097496 A1 | 4/2008 | Chang et al. |
| 2008/0108860 A1 | 5/2008 | Bell et al. |
| 2008/0134474 A1 | 6/2008 | Urysov |
| 2008/0171907 A1 | 7/2008 | Long et al. |
| 2008/0243106 A1 | 10/2008 | Coe et al. |
| 2008/0249534 A1 | 10/2008 | Gruber et al. |
| 2008/0269779 A1 | 10/2008 | Caddedu et al. |
| 2008/0300458 A1 | 12/2008 | Kim et al. |
| 2009/0005636 A1 | 1/2009 | Pang et al. |
| 2009/0004324 A1 | 2/2009 | Dominguez et al. |
| 2009/0043246 A1 | 2/2009 | Dominguez |
| 2009/0054909 A1 | 2/2009 | Farritor et al. |
| 2009/0062722 A1 | 3/2009 | Wakeford et al. |
| 2009/0076536 A1 | 3/2009 | Rentschler et al. |
| 2009/0137984 A1 | 5/2009 | Minnelli |
| 2009/0187074 A1 | 7/2009 | Saadat et al. |
| 2009/0192344 A1 | 7/2009 | Bakos et al. |
| 2009/0026771 A1 | 10/2009 | Baskett |
| 2009/0267717 A1 | 10/2009 | Baskett |
| 2009/0318762 A1 | 12/2009 | Segawa et al. |
| 2010/0010306 A1 | 1/2010 | Kawano et al. |
| 2010/0030026 A1 | 2/2010 | Uchiyama et al. |
| 2010/0036394 A1 | 2/2010 | Mintz et al. |
| 2010/0036399 A1 | 2/2010 | Viola |
| 2010/0081876 A1 | 4/2010 | Linenkugel et al. |
| 2010/0105984 A1 | 4/2010 | Brewer et al. |
| 2010/0113872 A1 | 5/2010 | Asada et al. |
| 2010/0114126 A1 | 5/2010 | Neff |
| 2010/0137845 A1 | 6/2010 | Ramstein et al. |
| 2010/0145147 A1 | 6/2010 | Pinsky et al. |
| 2010/0152539 A1 | 6/2010 | Ghabrial et al. |
| 2010/0160739 A1 | 6/2010 | Van Lue |
| 2010/0168523 A1 | 7/2010 | Duchame |
| 2010/0174234 A1 | 7/2010 | Werp et al. |
| 2010/0193566 A1 | 8/2010 | Scheib et al. |
| 2010/0204727 A1 | 8/2010 | Dominguez |
| 2010/0217245 A1 | 8/2010 | Prescott |
| 2010/0237206 A1 | 9/2010 | Barker |
| 2010/0256636 A1 | 10/2010 | Fernandez et al. |
| 2010/0268254 A1 | 10/2010 | Golden |
| 2010/0298645 A1 | 11/2010 | Deutch |
| 2011/0040152 A1 | 2/2011 | Kim et al. |
| 2011/0054306 A1 | 3/2011 | Del Nido et al. |
| 2011/0087223 A1 | 4/2011 | Spivey |
| 2011/0087224 A1 | 4/2011 | Cadeddu et al. |
| 2011/0087249 A1 | 4/2011 | Rodrigues et al. |
| 2011/0105848 A1 | 5/2011 | Sadovsky et al. |
| 2011/0121050 A1 | 5/2011 | Nicholas et al. |
| 2011/0130787 A1 | 6/2011 | Cinquin et al. |
| 2011/0184440 A1 | 7/2011 | Saldinger |
| 2011/0230726 A1 | 9/2011 | Viola |
| 2011/0276941 A1 | 11/2011 | Oi |
| 2011/0283822 A1 | 11/2011 | Caddedu et al. |
| 2011/0284014 A1 | 11/2011 | Cadeddu et al. |
| 2011/0285488 A1 | 11/2011 | Scott et al. |
| 2011/0295067 A1 | 12/2011 | Rodriguez Fernandez et al. |
| 2011/0306840 A1 | 12/2011 | Allen et al. |
| 2011/0313415 A1 | 12/2011 | Fernandez et al. |
| 2012/0016362 A1 | 1/2012 | Heinrich et al. |
| 2012/0035416 A1 | 2/2012 | Fernandez et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078292 A1 | 3/2012 | Banju |
| 2012/0008535 A1 | 4/2012 | Cadeddu et al. |
| 2012/0085358 A1 | 4/2012 | Cadeddu et al. |
| 2012/0101488 A1 | 4/2012 | Aldridge et al. |
| 2012/0116148 A1 | 5/2012 | Weinberg et al. |
| 2012/0227748 A1 | 9/2012 | Sanders |
| 2012/0238796 A1 | 9/2012 | Conlon |
| 2012/0330089 A1 | 12/2012 | Ritter et al. |
| 2013/0030462 A1 | 1/2013 | Keating et al. |
| 2013/0066304 A1 | 3/2013 | Belson et al. |
| 2013/0085341 A1 | 4/2013 | Nobis et al. |
| 2013/0090666 A1 | 4/2013 | Hess et al. |
| 2013/0109267 A1 | 5/2013 | Schweikardt et al. |
| 2013/0110128 A1 | 5/2013 | Schostek et al. |
| 2013/0123828 A1 | 5/2013 | Culmer et al. |
| 2013/0158348 A1 | 6/2013 | Nobis et al. |
| 2013/0158523 A1 | 6/2013 | Bergs et al. |
| 2013/0158659 A1 | 6/2013 | Bergs et al. |
| 2013/0158660 A1 | 6/2013 | Bergs et al. |
| 2013/0172672 A1 | 7/2013 | Iddan et al. |
| 2013/0172906 A1 | 7/2013 | Olson et al. |
| 2013/0226226 A1 | 8/2013 | Garrison et al. |
| 2013/0245356 A1 | 9/2013 | Fernandez et al. |
| 2013/0253256 A1 | 9/2013 | Griffith et al. |
| 2013/0253275 A1 | 9/2013 | Ransden et al. |
| 2013/0253550 A1 | 9/2013 | Beisel et al. |
| 2013/0267788 A1 | 10/2013 | Duan et al. |
| 2013/0289579 A1 | 10/2013 | Yeung et al. |
| 2013/0289768 A1 | 10/2013 | Yeung et al. |
| 2013/0303851 A1 | 11/2013 | Griffith et al. |
| 2014/0066695 A1 | 3/2014 | Deutch |
| 2014/0084761 A1 | 3/2014 | Scott et al. |
| 2014/0135616 A1 | 5/2014 | Stein et al. |
| 2014/0187857 A1 | 7/2014 | Wilson et al. |
| 2014/0243586 A1 | 8/2014 | Rohaninejad et al. |
| 2014/0243597 A1 | 8/2014 | Weisenburgh, II et al. |
| 2014/0257370 A1 | 9/2014 | Taylor et al. |
| 2014/0276335 A1 | 9/2014 | Pate |
| 2014/0276841 A1 | 9/2014 | Rodriguez-Navarro et al. |
| 2014/0277104 A1 | 9/2014 | Rodriguez-Navarro et al. |
| 2014/0350574 A1 | 11/2014 | Farritor et al. |
| 2014/0358229 A1 | 12/2014 | Bergs et al. |
| 2015/0012010 A1 | 1/2015 | Adler et al. |
| 2015/0230801 A1 | 8/2015 | Rodriguez et al. |
| 2016/0038135 A1 | 2/2016 | Deutch |
| 2016/0120613 A1 | 5/2016 | Cadeddu et al. |
| 2016/0228138 A1 | 8/2016 | Rodriguez-Navarro et al. |
| 2016/0302811 A1 | 10/2016 | Nobis et al. |
| 2018/0153633 A1 | 6/2018 | Rodriguez-Navarro et al. |
| 2018/0271603 A1 | 9/2018 | Nir et al. |
| 2018/0296289 A1 | 10/2018 | Rodriguez-Navarro et al. |
| 2018/0325604 A1 | 11/2018 | Atarot et al. |
| 2019/0133631 A1 | 5/2019 | Rodriguez-Navarro et al. |
| 2019/0269394 A1 | 9/2019 | Deutch |
| 2020/0289140 A1 | 9/2020 | Rodriguez-Navarro et al. |
| 2021/0290330 A1 | 9/2021 | Rodriguez-Navarro et al. |

FOREIGN PATENT DOCUMENTS

| | | |
|---|---|---|
| CN | 2244381 | 1/1997 |
| CN | 101090672 | 12/2007 |
| CN | 201079412 | 7/2008 |
| CN | 201091596 | 7/2008 |
| CN | 102355865 | 2/2012 |
| CN | 203953720 U | 11/2014 |
| CN | 102068288 | 4/2015 |
| CN | 101534725 | 9/2019 |
| DE | 4212430 | 10/1993 |
| DE | 19534618 | 3/1997 |
| DE | 102005006705 | 8/2006 |
| DE | 10-2010-010417 A1 | 9/2011 |
| EP | 2366357 | 1/1945 |
| EP | 2391277 | 11/1979 |
| EP | 1797823 | 6/2007 |
| EP | 2 012 697 A2 | 1/2009 |
| EP | 1972284 | 9/2009 |
| EP | 2 355 699 A2 | 8/2011 |
| EP | 2 381 873 A2 | 11/2011 |
| EP | 1942810 | 8/2012 |
| EP | 2 571 443 A2 | 3/2013 |
| EP | 2595548 | 5/2013 |
| EP | 2 842 511 A1 | 3/2015 |
| JP | 09-192137 | 7/1997 |
| JP | 2004-357816 A | 12/2004 |
| JP | 2005021576 | 1/2005 |
| JP | 4320214 | 8/2009 |
| JP | 2009-538699 | 11/2009 |
| WO | WO200051500 | 9/2000 |

(56) References Cited

FOREIGN PATENT DOCUMENTS

| | | |
|---|---|---|
| WO | WO-2005/004734 A1 | 1/2005 |
| WO | WO-2005/032370 A1 | 4/2005 |
| WO | 2006071120 | 7/2006 |
| WO | WO2007067231 | 6/2007 |
| WO | WO-2007/130382 A2 | 11/2007 |
| WO | WO-2007/130382 A3 | 11/2007 |
| WO | 2007142977 A2 | 12/2007 |
| WO | WO-2007/143162 A2 | 12/2007 |
| WO | WO-2007/143162 A3 | 12/2007 |
| WO | WO-2007/143170 A2 | 12/2007 |
| WO | WO-2007/143170 A3 | 12/2007 |
| WO | WO2007142977 | 12/2007 |
| WO | 2008/039237 | 4/2008 |
| WO | WO2008085919 | 7/2008 |
| WO | 2008131128 | 10/2008 |
| WO | WO-2009/008865 A1 | 1/2009 |
| WO | 2009019288 | 2/2009 |
| WO | 2009070743 | 6/2009 |
| WO | WO-2010/056716 A2 | 5/2010 |
| WO | WO-2010/056716 A3 | 5/2010 |
| WO | WO-2010/077561 A1 | 7/2010 |
| WO | WO-2010/083480 A2 | 7/2010 |
| WO | WO-2010/083480 A3 | 7/2010 |
| WO | 2010-089635 | 8/2010 |
| WO | WO-2011/044468 A2 | 4/2011 |
| WO | WO-2011/044468 A3 | 4/2011 |
| WO | WO-2011/044471 A2 | 4/2011 |
| WO | WO-2011/044471 A3 | 4/2011 |
| WO | 2011091483 | 8/2011 |
| WO | WO-2011/146691 A2 | 11/2011 |
| WO | WO-2011/146691 A3 | 11/2011 |
| WO | WO2011/146698 A2 | 11/2011 |
| WO | WO2011/146698 A3 | 11/2011 |
| WO | WO-2011/146709 A2 | 11/2011 |
| WO | WO-2011/146709 A3 | 11/2011 |
| WO | 2012010910 | 1/2012 |
| WO | WO-2012/031114 A2 | 3/2012 |
| WO | WO-2012/031114 A3 | 3/2012 |
| WO | WO-2012/033925 A1 | 3/2012 |
| WO | WO-2012/048102 A2 | 4/2012 |
| WO | WO-2012/048102 A3 | 4/2012 |
| WO | WO-2013/096470 A1 | 6/2013 |
| WO | WO-2014/133751 A1 | 9/2014 |
| WO | 2014159023 | 10/2014 |
| WO | 2014163872 | 10/2014 |
| WO | 2015112645 | 7/2015 |
| WO | WO-2015/142953 A1 | 9/2015 |
| WO | 2016168380 | 10/2016 |

OTHER PUBLICATIONS

Patent Trial and Appeal Board, IPR2019-01295, U.S. Pat. No. 8,602,981, Decision Granting Institution of Inter Partes Review, Jan. 22, 2020.
Patent Trial and Appeal Board, IPR2019-01294, Preliminary Guidance in response to Patent Owner's Motion to Amend, Aug. 17, 2020.
Patent Trial and Appeal Board, IPR2019-01295, U.S. Pat. No. 8,602,981, Preliminary Guidance in response to Patent Owner's Motion to Amend, Aug. 17, 2020.
Second Declaration of Raul Fernandez filed with Case No. IPR2019-01295, EX1025, dated Jul. 22, 2020.
Petitioner's Reply to Patent Owner's Response, Inter Partes Review of U.S. Pat. No. 8,602,981, Case No. IPR2019-01295, dated Jul. 22, 2020.
Petitioner's Opposition to Patent Owner's Motion to Amend, Inter Partes Review of U.S. Pat. No. 8,602,981, Case No. IPR2019-01295, dated Jul. 22, 2020.
Petitioner's Reply to Patent Owner's Response, Inter Partes Review of U.S. Pat. No. 9,386,373, Case No. IPR2019-01294, dated Jul. 22, 2020.
Petitioner's Opposition to Patent Owner's Motion to Amend, Inter Partes Review of U.S. Pat. No. 9,386,973, Case No. IPR2019-01294, dated Jul. 22, 2020.
Second Declaration of Raul Fernandez filed with Case No. IPR2019-01294, EX1025, dated Jul. 22, 2020.
Patent Owner's Response, Inter Partes Review of U.S. Pat. No. 8,602,981, Case No. IPR2019-01295, dated Apr. 29, 2020.
Patent Owner's Response, Inter Partes Review of U.S. Pat. No. 9,386,973, Case No. IPR2019-01294, dated Apr. 29, 2020.
Patent Owner's Revised Contingent Motion to Amend, Inter Partes Review of U.S. Pat. No. 8,602,981, Case No. IPR2019-01295, dated Sep. 2, 2020.
Patent Owner's Revised Contingent Motion to Amend, Inter Partes Review of U.S. Pat. No. 9,386,973, Case No. IPR2019-01294, dated Sep. 2, 2020.
Aesculap, "Endoscopic Vascular surgery in the pelvic region," B/Braun, Aesculap AG & CO.KG, Catalog, 48 pages, 2006, http://web.archive.org/web/20060313094452/http:// www.tmml.com/Catalogue/SellSheets/A19INFO_ENDOSCOPIC_VASCULAR_SURGERY.pdf.
Australian Patent Examination Report dated May 20, 2013 in AU Application No. 2008329676 (3 pages).
European Search Report dated May 23, 2013 in EP Application No. 08853840.0 (4 pages).
Park et al., "Trocar-less instrumentation for laparoscopy magnetic positioning of intra-abdominal camera and retractor," Annal of Surgery, vol. 245, pp. 379-384 (2007).
International Search Report and Written Opinion Issued by the U.S. Patent and Trademark Office as International Searching Authority for International Application No. PCT/US2008/084991 dated Apr. 9, 2009 (4 pages).
Petition for Inter Partes Review of U.S. Pat. No. 8,602,981, Case No. IPR2019-01295, dated Jul. 1, 2019.
Declaration of Raul Fernandez filed with Case No. IPR2019-01295, dated Jul. 1, 2019.
Cadeddu et al., Transabdominal Magnetic Anchoring System for Trocar-Less Laparoscopic Surgery, J. Urology, vol. 167, No. 4, Supplement, May 25, 2002.
Park et al., Trocar-less Instrumentation for Laparoscopy, Surgical Technique, vol. 245, No. 3, Mar. 2007.
Zeltser et al., Single Trocar Laparoscopic Nephrectomy Using Magnetic Anchoring and Guidance System in the Porcine Model, J. Urology, vol. 178, Jul. 2007.
Scott et al., Completely transvaginal NOTES cholecystectomy using magnetically anchored instruments, Surg. Endosc, 2007, 21:2308-2316.
Duchene et al., Magnetic Position System for Trocarless Laparoscopic Instruments, J. Endourology, vol. 18, No. 7, Sep. 2004.
Odwin et al., Prove Covers and Disinfectants for Transvaginal Transducers, JDMS, 6:130-135, May/Jun. 1990.
Milki et al., Vaginal ultrasound probe cover leakage: implications for patient care, Fertility and Sterility, American Society for Reproductive Medicine, vol. 69, No. 3, Mar. 1998.
Petition for Inter Partes Review of U.S. Pat. No. 9,386,973, Case No. IPR2019-01294, dated Jul. 1, 2019.
Declaration of Raul Fernandez filed with Case No. IPR2019-01294, dated Jul. 1, 2019.
Dominguez, Guillermo M., "Colecistectomia Con un Trocar Asistida Por Imanes De Neodimio. Reporte de un Caso", Asociacion Mexicana de Cirugia Edoscopica, A.C., vol. 8, No. 4, Oct.-Dec. 2007, pp. 172-176.
Wikipedia (2015). "Stainless Steel," retrieved from https://en.wikipedia.org/wiki/Stainless-steel, 13 pages.
Best, S.L. et al. (2010). "Development of magnetic anchoring and guidance systems for minimally invasive surgery," Indian J. of Urology 26:418-422.
Best, S.L. et al. (2010). "Solo Surgeon LESS Nephrectomy Facilitated by New Generation Magnetically Anchored and Guided (MAGS) Camera," World Congress of Endourology, PS38-14, Chicago IL, Sep. 2010.

(56) References Cited

OTHER PUBLICATIONS

Best, S.L. et al. (2010). "MAGS Instrumentation for LESS/NOTES: Lack of Histologic Damage After Prolonged Magnetic Coupling Across the Abdominal Wall," World Congress of Endourology, PS2-4, Chicago IL, Sep. 2010.
Best, S.L. et al. (2008). "Maximizing Coupling Strength of Magnetically Anchored NOTES Instruments: How Thick Can We Go?" Surgical Endoscopy, vol. 22: S241.
Cadeddu, J. et al. (2009). "Novel Magnetically Guided Intraabdominal Camera to Facilitate Laparoendoscopic Single Site Surgery: Initial Human Experience," Surgical Endoscopy 23:1894-1899.
Dominguez, G. et al. (2009). "Retraction and triangulation with neodymium magnetic forceps for single-port laparoscopic cholecystectomy," Surg. Endosc. 23:1660-1666.
Extended European Search Report dated Jul. 20, 2016, for EP Application No. 14 778 895.4, filed on Feb. 25, 2014, 7 pages.
Extended European Search Report dated Dec. 20, 2016, for EP Application No. 09 839 564.3, filed on Oct. 1, 2009, 11 pages.
Extended European Search Report dated Sep. 27, 2017, for EP Application No. 15 741 055.6, filed on Jan. 21, 2015, 9 pages.
Extended European Search Report dated Oct. 30, 2018, for EP Application No. 16 780 691.8, filed on Apr. 13, 2016, 6 pages.
Extended European Search Report dated Nov. 26, 2018, for EP Application No. 16 780 688.4, filed on Sep. 26, 2017, 9 pages.
Extended European Search Report dated Aug. 22, 2019, for EP Application No. 17 736 483.3, filed on Jan. 6, 2017, 8 pages.
Fernandez, R. et al. (2012). "Determining a Performance Envelope for Capture of Kidney Stones Functionalized with Superparamagnetic Particles," Journal of Endourology, 26(9):1227-30.
Fernandez, R. et al. (2003). "Development of a Transabdominal Anchoring System for Trocar-Less Laparoscopic Surgery," Advances in Bioengineering—ASME International Mechanical Engineering Congress & Exposition, Washington DC, Nov. 2003, BED vol. 55, pp. 157-158.
Final Office Action dated Sep. 16, 2016, for U.S. Appl. No. 14/704,828, filed May 5, 2015, 10 pages.
Final Office Action dated Jan. 25, 2016, for U.S. Appl. No. 14/337,082, filed Jul. 21, 2014, 9 pages.
Final Office Action dated Dec. 28, 2016, for U.S. Appl. No. 14/200,302, filed Mar. 7, 2014, 15 pages.
Final Office Action dated Sep. 6, 2017, for U.S. Appl. No. 14/200,302, filed Mar. 7, 2014, 9 pages.
Final Office Action dated Mar. 7, 2018, for U.S. Appl. No. 15/098,262, filed Apr. 13, 2016, 10 pages.
Final Office Action dated Feb. 26, 2019, for U.S. Appl. No. 15/195,898, filed Jun. 28, 2016, 9 pages.
Final Office Action dated Nov. 25, 2020, for U.S. Appl. No. 15/728,297, filed Oct. 9, 2017, 11 pages.
International Search Report dated Jul. 30, 2014, for PCT Application No. PCT/US2014/021537, filed on Mar. 7, 2014, 2 pages.
International Search Report for International Application No. PCT/IB2009/054307 dated Feb. 8, 2010, 4 pages.
International Search Report dated May 4, 2015, for PCT Application No. PCT/US2015/012319, filed on Jan. 21, 2015, 2 pages.
International Search Report dated Jul. 18, 2014, for PCT Application No. PCT/US2014/018307, filed on Feb. 25, 2014, 4 pages.
International Search Report dated Jul. 15, 2016, for PCT Application No. PCT/US2016/027385, filed on Apr. 13, 2016, 2 pages.
International Search Report dated Aug. 22, 2016, for PCT Application No. PCT/US2016/027390, filed on Apr. 13, 2016, 4 pages.
International Search Report dated Apr. 3, 2017, for PCT Application No. PCT/US2017/012628, filed on Jan. 6, 2017, 2 pages.
Leong, F. et al. (2016). "Magnetic surgical instruments for robotic abdominal surgery," IEEE Reviews in Biomedical Engineering 9:66-78.
Mashaud, L. et al. (2011). "Tissue Compression Analysis for Magnetically Anchored Cautery Dissector During Single Site Laparoscopic Cholecystectomy," Journal of Gastrointestinal Surgery 15:902-907.
Mashaud, L. et al. (2010). "Tissue Compression Analysis for Magnetically Anchored Cautery Dissector During Single Site Laparoscopic Cholecystectomy," Gastroenterology, 138:5 (Supplement 1):S-882.
Mashaud, L. et al. (2010). "Magnetic Cautery Dissector Suitability for Traditional or Single Site Laparoscopic Cholecystectomy in Human Cadaver Models," 12th World Congress of Endoscopic Surgery, p. 246, National Harbor, MD, Apr. 2010.
Non-Final Office Action dated May 25, 2016, for U.S. Appl. No. 14/200,302, filed Mar. 7, 2014, 12 pages.
Non-Final Office Action dated May 21, 2013 for U.S. Appl. No. 13/132,185, filed Aug. 17, 2011, 18 pages.
Non-Final Office Action dated Jul. 21, 2016, for U.S. Appl. No. 14/337,082, filed Jul. 21, 2014, 9 pages.
Non-Final Office Action dated Jul. 13, 2015, for U.S. Appl. No. 14/337,082, filed Jul. 21, 2014, 10 pages.
Non-Final Office Action dated Jan. 25, 2016, for U.S. Appl. No. 14/704,828, filed May 5, 2015, 9 pages.
Non-Final Office Action dated Jul. 14, 2015, for U.S. Appl. No. 14/704,828, filed May 5, 2015, 10 pages.
Non-Final Office Action dated Oct. 24, 2013, for U.S. Appl. No. 14/019,370, filed Sep. 5, 2013, 7 pages.
Non-Final Office Action dated Oct. 22, 2015, for U.S. Appl. No. 14/019,404, filed Sep. 5, 2013, 6 pages.
Non-Final Office Action dated May 22, 2017, for U.S. Appl. No. 14/200,302, filed Mar. 7, 2014, 14 pages.
Non-Final Office Action dated May 3, 2017, for U.S. Appl. No. 14/704,828, filed May 5, 2015, 8 pages.
Non-Final Office Action dated Jul. 24, 2017, for U.S. Appl. No. 15/098,262, filed Apr. 13, 2016, 9 pages.
Non-Final Office Action dated Jun. 29, 2018, for U.S. Appl. No. 15/195,898, filed Jun. 28, 2016, 9 pages.
Non-Final Office Action dated Sep. 17, 2019, for U.S. Appl. No. 15/728,297, filed Oct. 9, 2017, 8 pages.
Non-Final Office Action dated Mar. 3, 2020, for U.S. Appl. No. 15/728,302, filed Oct. 9, 2017, 14 pages.
Non-Final Office Action dated Mar. 6, 2020, for U.S. Appl. No. 15/926,578, filed Mar. 20, 2018, 9 pages.
Non-Final Office Action dated Dec. 22, 2020, for U.S. Appl. No. 16/149,576, filed Oct. 2, 2018, 10 pages.
Non-Final Office Action dated May 12, 2021, for U.S. Appl. No. 16/008,976, filed Jun. 14, 2018, 15 pages.
Non-Final Office Action dated Apr. 29, 2021, for U.S. Appl. No. 16/419,363, filed May 22, 2019, 9 pages.
Notice of Allowance dated Feb. 14, 2014, for U.S. Appl. No. 14/019,370, filed Sep. 5, 2013, 7 pages.
Notice of Allowance dated Mar. 14, 2014, for U.S. Appl. No. 13/132,185, filed Aug. 17, 2011, 7 pages.
Notice of Allowance dated Mar. 14, 2016, for U.S. Appl. No. 14/019,404, filed Sep. 5, 2013, 7 pages.
Notice of Allowance dated May 3, 2017, for U.S. Appl. No. 14/337,082, filed Jul. 21, 2014, 7 pages.
Notice of Allowance dated Aug. 25, 2017, for U.S. Appl. No. 14/337,082, filed Jul. 21, 2014, 7 pages.
Notice of Allowance dated Nov. 22, 2017, for U.S. Appl. No. 14/200,302, filed Mar. 7, 2014, 5 pages.
Notice of Allowance dated Jan. 19, 2018, for U.S. Appl. No. 14/704,828, filed May 5, 2015, 7 pages.
Notice of Allowance dated Aug. 24, 2018, for U.S. Appl. No. 15/098,262, filed Apr. 13, 2016, 9 pages.
Notice of Allowance dated Sep. 11, 2019, for U.S. Appl. No. 15/195,898, filed Jun. 28, 2016, 9 pages.
Notice of Allowance dated Nov. 26, 2019, for U.S. Appl. No. 15/195,898, filed Jun. 28, 2016, 6 pages.
Notice of Allowance dated Sep. 29, 2020, for U.S. Appl. No. 15/728,302, filed Oct. 9, 2017, 8 pages.
Notice of Allowance dated Feb. 5, 2021, for U.S. Appl. No. 15/926,578, filed Mar. 20, 2018, 9 pages.
Raman, J. (2009). "Complete Transvaginal NOTES Nephrectomy Using Magnetically Anchored Instrumentation," Journal of Endourology 23:367-371.
Rivas, H. et al. (2005). "A Magnetic Positioning System to Drive Trocarless Laparoscopic Instruments," First International Mini-

(56) References Cited

OTHER PUBLICATIONS mally Invasive Robotic Association (MIRA) Conference on Robotic Surgery, Innsbruck, Austria, Dec. 2005.
Scott, D. et al. (2008). "Optimizing Magnetically Anchored Camera, Light Source, Graspers, and Cautery Dissector for Transvaginal NOTES Cholecystectomy," Surgical Endoscopy 22:S244.
Scott, D. et al. (2008). "Randomized Comparison of Laparoscopic, Flexible Endoscopic, and Wired and Wireless Magnetic NOTES Cameras on Ex-Vivo and In-Vivo Surgical Performance," Gastrointestinal Endoscopy, vol. 67: AB115.
Scott, D. et al. (2008). "Transvaginal Single Access "Pure" NOTES Sleeve Gastrectomy Using a Deployable Magnetically Anchored Video Camera," Gastrointestinal Endoscopy, vol. 67: AB116.
Scott, D. et al. (2007). "Transgastric, Transcolonic, and Transvaginal Cholecystectomy Using Magnetically Anchored Instruments," Surgical Endoscopy, vol. 21: S474.
Scott, D. et al. (2007). "Completely Transvaginal Cholecystectomy Using Magnetically Anchored Instruments," Surgical Endoscopy, vol. 21: S335.
Scott, D. et al. (2007). "Short-Term Survival Outcomes Following Transvaginal NOTES Cholecystectomy Using Magnetically Anchored Instruments," Gastrointestinal Endoscopy, vol. 65: AB109.
Supplemental Notice of Allowability dated Dec. 18, 2020, for U.S. Appl. No. 15/728,302, filed Oct. 9, 2017, 3 pages.
Swain, C. et al. (2008). "Linear Stapler Formation of Ileo-Rectal, Entero-Enteral and Gastrojejunal Anastomoses During Dual and Single Access "Pure" NOTES Procedures: Methods, Magnets and Stapler Modifications," Gastrointestinal Endoscopy, vol. 67: AB119.
Swain, P. et al. (2008). "Wireless Endosurgery for NOTES," Gastrointestinal Endoscopy, vol. 67: AB104.
Tan, Y. (2011). "Modeling of Magnetic Tools for Use with Superparamagnetic Particles for Magnetic Stone Extraction," 26th Engineering & Urology Society Annual Meeting, p. 29, Washington DC, May 14, 2011.
Tan, Y. (2012). "In Vitro Comparison of Prototype Magnetic Tool with Conventional Nitinol Basket for Ureteroscopic Retrieval of Stone Fragments Rendered Paramagnetic with Iron-Oxide Microparticles," The Journal of Urology, vol. 187, Issue 4, pp. e857-e858.
Tang, S. (2008). "Live Video Manipulator for Endoscopy and NOTES," Gastrointestinal Endoscopy 68:559-564.
Tillander, H. (1951). "Magnetic guidance of a catheter with articulated steel tip," Acta Radiologica pp. 62-64.
Written Opinion of the International Searching Authority dated Jul. 30, 2014, for PCT Application No. PCT/US2014/021537, filed on Mar. 7, 2014, 5 pages.
Written Opinion of the International Searching Authority for International Application No. PCT/IB2009/054307 dated Feb. 8, 2010.
Written Opinion of the International Searching Authority dated Jul. 18, 2014, for PCT Application No. PCT/US2014/018307, filed on Feb. 25, 2014, 5 pages.
Written Opinion of the International Searching Authority dated May 4, 2015, for PCT Application No. PCT/US2015/012319, filed on Jan. 21, 2015, 5 pages.
Written Opinion of the International Searching Authority dated Jul. 15, 2016, for PCT Application No. PCT/US2016/027385, filed on Apr. 13, 2016, 11 pages.
Written Opinion of the International Searching Authority dated Aug. 22, 2016, for PCT Application No. PCT/US2016/027390, filed on Apr. 13, 2016, 9 pages.
Written Opinion of the International Searching Authority dated Apr. 3, 2017, for PCT Application No. PCT/US2017/012628, filed on Jan. 6, 2017, 7 pages.
U.S. Appl. No. 61/113,495, filed Nov. 25, 2008, by Fernandez et al.
Final Office Action dated Sep. 3, 2021, for U.S. Appl. No. 16/149,576, filed Oct. 2, 2018, 14 pages.
Final Office Action dated Oct. 26, 2021, for U.S. Appl. No. 16/419,363, filed May 22, 2019, 7 pages.
Final Office Action dated Feb. 7, 2022, for U.S. Appl. No. 16/008,976, filed Jun. 14, 2018, 20 pages.
Non-Final Office Action dated Sep. 15, 2021, for U.S. Appl. No. 15/728,297, filed Oct. 9, 2017, 11 pages.
Notice of Allowance dated Feb. 14, 2022, for U.S. Appl. No. 16/149,576, filed Oct. 2, 2018, 9 pages.

\* cited by examiner

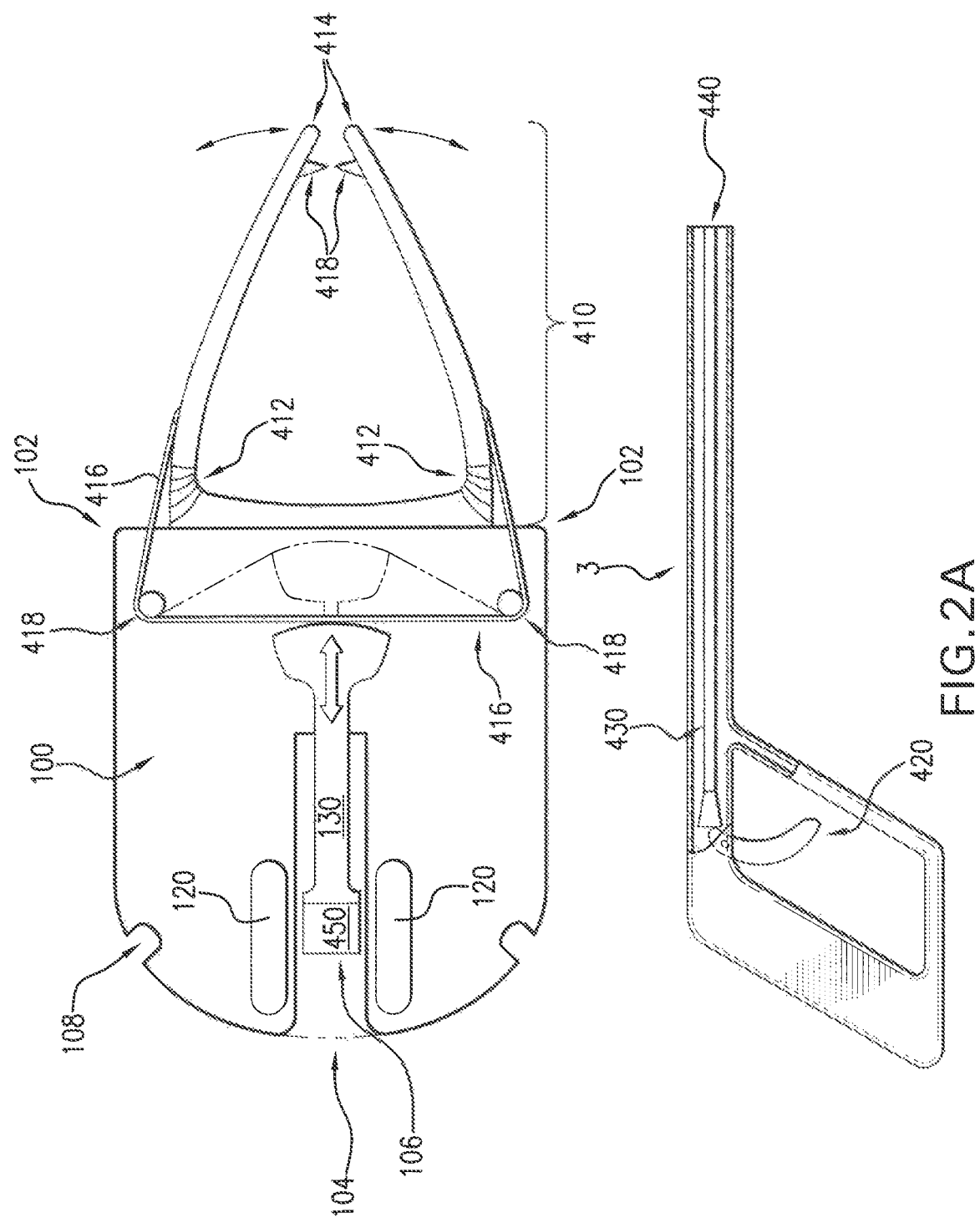

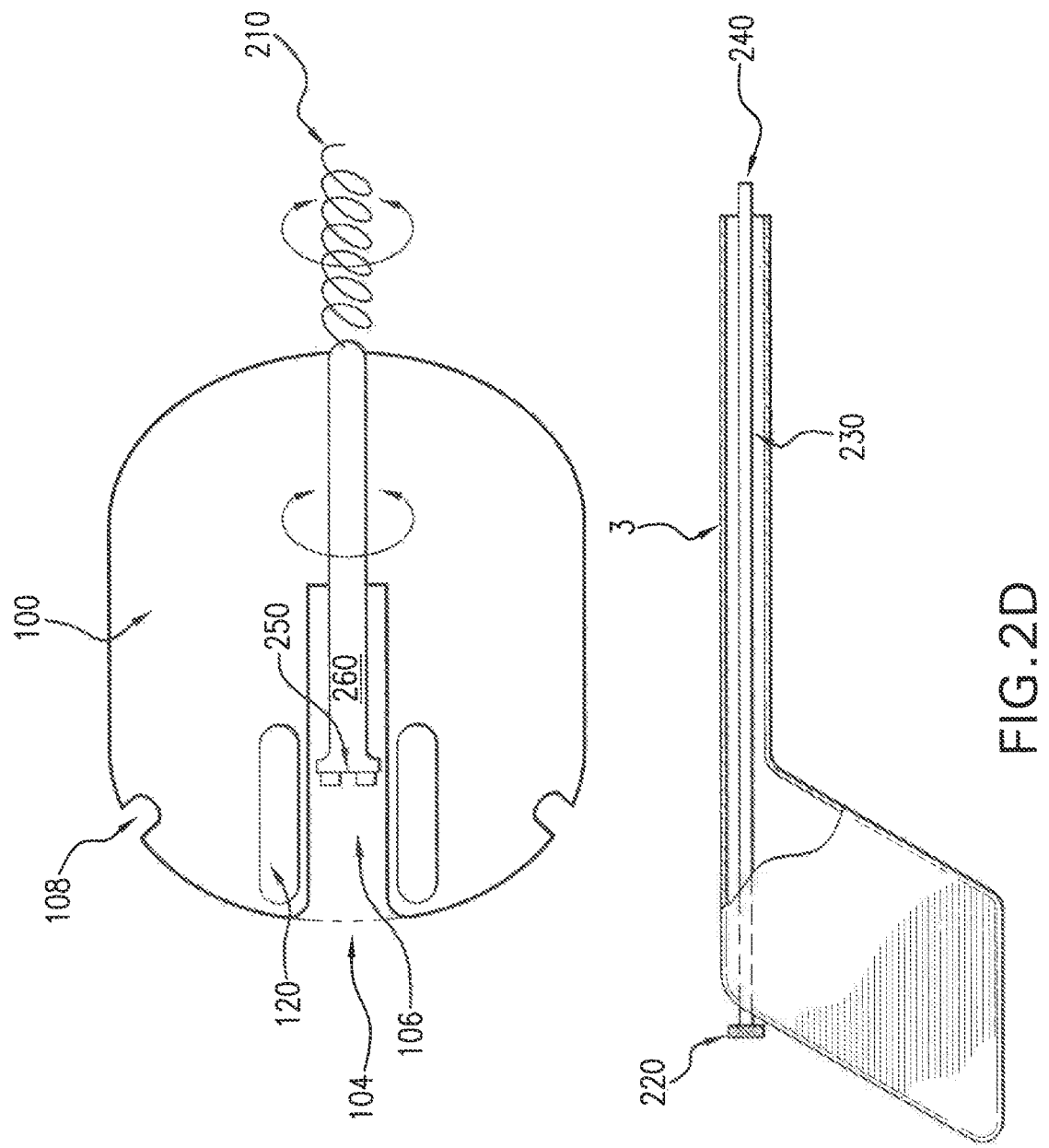

MAGNARETRACTOR SYSTEM AND METHOD

CROSS-REFERENCE TO RELATED APPLICATIONS

This application is a Continuation of co-pending U.S. application Ser. No. 16/419,363, filed May 22, 2019, which is a Continuation of U.S. patent application Ser. No. 15/966,958, filed Apr. 30, 2018, now U.S. Pat. No. 10,335,134, which is a Continuation of U.S. patent application Ser. No. 14/918,974, filed Oct. 21, 2015, now U.S. Pat. No. 9,962,148, which is a Continuation of U.S. patent application Ser. No. 14/074,783, filed Nov. 8, 2013, now U.S. Pat. No. 9,386,973, which is a Continuation of U.S. patent application Ser. No. 12/787,998, filed May 26, 2010, now U.S. Pat. No. 8,602,981, which is a Continuation-in-Part of International Application PCT/US08/84991, filed Nov. 26, 2008, which claims the benefit of U.S. Provisional Application 60/996,575, filed Nov. 26, 2007, the contents of each of which are incorporated by reference herein.

FIELD OF INVENTION

The present invention is directed generally to surgical apparatus, systems and methods for use in subjects including humans and animals, and to apparatus, systems and methods of manipulating objects within the body of a subject when performing laparoscopy.

BACKGROUND OF INVENTION

When performing laparoscopic surgery in a body cavity such as the abdomen, the number of surgical instruments which can be manipulated in the abdomen is limited by the number of abdominal ports incised. Accordingly, the number of organs and tissues the surgeon can manipulate simultaneously is limited by the number of instruments in place.

In a standard laparoscopy for endometriosis, for example, a camera is placed through the umbilical port, and two lower quadrant ports are made for use with instruments. In order to access, excise or fulgurate endometriosis deep in the pelvis or behind an ovary, the ovary must be retracted. An instrument is inserted into one port and used for the purpose of grasping and retracting the ovary. It is often difficult to control the ovary with the grasper, often resulting in unwanted and uncontrolled movement of the ovary. With the camera inserted through the umbilical port and the grasper inserted through a second port, there is only one port left available to the surgeon. Since there is only one port available, the process of fulgurating or excising the endometrial implants is thereby made more difficult, because in order to avoid damaging the underlying tissues, the peritoneum must be tented up. The surgeon must tent the peritoneum and fulgurate or excise the endometrial implants with a single instrument, or alternatively, incise one or more additional ports. The addition of operating instruments then will require the surgeon to relinquish control of the grasper since only two instruments can be manipulated at one time.

However, additional ports and instruments are not desirable for many reasons. Every additional port requires an accompanying abdominal incision, which pierces the peritoneum and abdominal muscles, and increases the risk of striking a blood vessel and infection. Furthermore, each incision carries cosmetic implications for the patient, as a visible scar may be formed.

In addition to the problem of adding ports to allow additional instruments into the abdominal cavity, there is a problem of limited workspace within the abdominal cavity. As more instruments are introduced into the abdomen, the area can become congested. With this congestion, instruments may inadvertently block or bump into each other, making the procedure more difficult for the surgeon and increasing the risk for the patient.

For example, in a laparoscopic hysterectomy, it is often difficult to retract the uterus in the beneficial manner possible in an open abdominal hysterectomy. In an open abdominal hysterectomy, a cork screw tool is often placed in the fundus of the uterus and used for upward traction in order to decrease bleeding. The traction on the uterus also makes it easier to access the lateral sides of the uterus and suture and ligate the uterine arteries and cardinal ligaments. To do this laparoscopically, the surgeon must try and place an extra port and use a grasper to retract the uterus—often a very difficult task. Additionally, the extra grasper often causes instrument clutter with the other instruments being used to carry out the dissection.

Furthermore, the surgeon is physically limited to controlling two instruments at a time, i.e., one instrument per hand. If it is elected to use an additional instrument to perform a function such as retraction of an ovary or manipulation of the uterus, the surgeon will encounter the problem of not being able to manipulate all of the instruments simultaneously.

In light of these problems, it would be desirable to have a laparoscopic system whereby a surgeon might retract and manipulate intra-abdominal organs and objects without the necessity of placing extra ports, as well as having the ability to gain better control over organs and perform functions currently not possible laparoscopically. It would also be desirable to have a system whereby a surgeon might manipulate intra-abdominal organs and objects without the added congestion of the abdominal cavity associated with the introduction of additional intra-abdominal instruments.

SUMMARY OF THE INVENTION

The present invention is a laparoscopic surgical method and system using magnetic fields such as those produced by magnets and tools responsive to these magnetic fields to allow a surgeon to retract and control intra-abdominal organs and objects without the necessity of having to place additional items in the abdominal cavity.

The system uses various fasteners such as screws, loops, clips, clamps etc., to attach to objects and organs within the body. These fasteners are capable of being influenced or manipulated in three-dimensional space, directly or indirectly, by a magnetic or electromagnetic field, to allow the surgeon to control intra-abdominal organs and objects without placing additional abdominal ports. The fasteners are then detached from the long tool used to place them into the abdomen. Then, an apparatus containing a magnetic field source, such as a magnet or electromagnet, is placed on the outside of the abdomen. The magnetic field produced by this apparatus is used to manipulate the fasteners attached to the objects or organs inside the abdomen, allowing the surgeon to retract or position the object around the abdomen without the use of an intra-abdominal instrument or placing additional ports.

BRIEF DESCRIPTION OF THE DRAWINGS

The present invention will be understood and appreciated more fully from the following detailed description, taken in conjunction with the drawings in which:

FIG. 2A is an embodiment of an intracorporeal apparatus;

FIG. 2D is an alternative embodiment of an intracorporeal apparatus with a screw mechanism, for conversion into rotational energy;

DETAILED DESCRIPTION OF THE INVENTION

The present invention provides laparoscopic surgeons a system and method to allow the surgeon to retract and manipulate intra-abdominal organs and objects without placing extra ports. Furthermore, the present invention allows the surgeon to maintain increased control over his instruments due to increased space in the body cavity.

Figure 1:
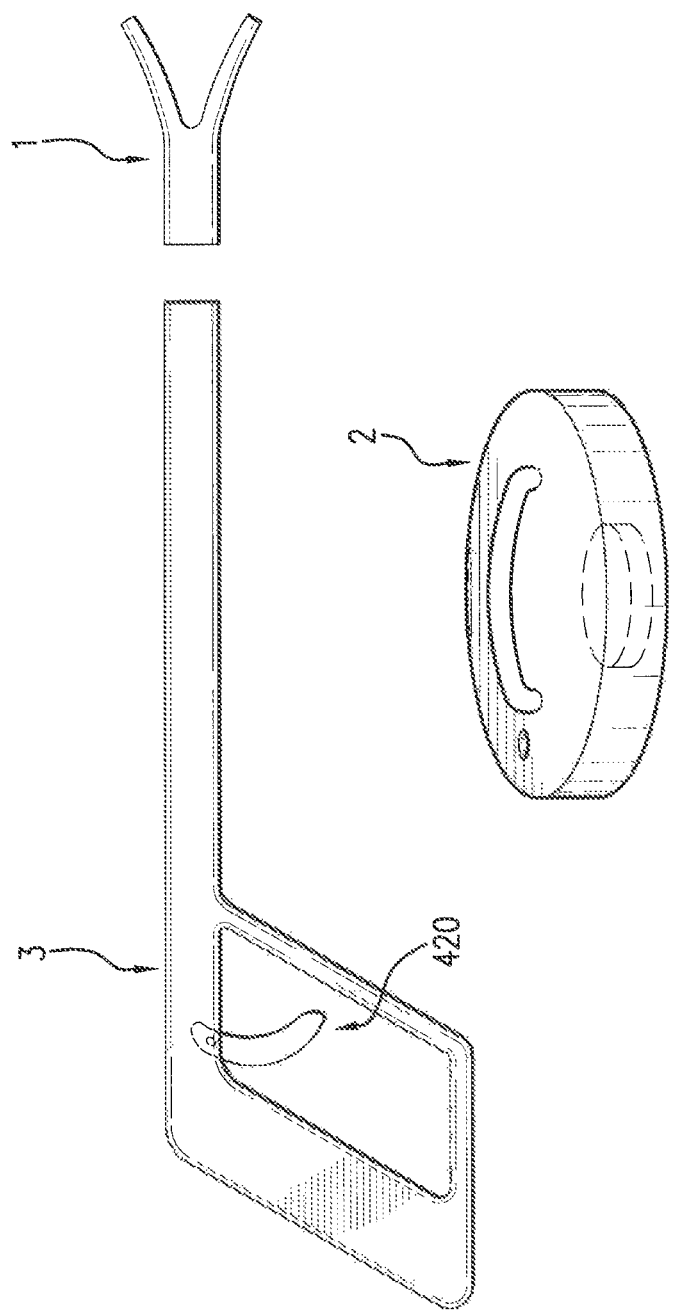
FIG. 1 is an embodiment of an intracorporeal, extracorporeal and placement apparatuses.

In a preferred embodiment, the system of the invention performs its functions with three classes of magnaretractor apparatuses working together—the intracorporeal apparatus 1, extracorporeal apparatus 2, and placement apparatus 3. See FIG. 1

The intracorporeal apparatuses are the set of tools that are used to attach to an object or tissue inside a patient's body. They are designed to interact with the placement apparatus to place it in the correct position inside the body, an extracorporeal apparatus to manipulate it from outside the body, and the object or tissue the surgeon wishes to manipulate. FIG. 2A shows a preferred embodiment of an intracorporeal apparatus. The preferred embodiment comprises a body 100 of some shape such as a narrow shaft at least in one cross section having a size no greater than a trocar. This is necessary as the intracorporeal apparatus in its preferred method of use will be passed through a trocar port into the patient's body. At one end 102 of the intracorporeal apparatus body, the apparatus is adapted to attach to an object or tissue. At the opposing end 104 of the body, the apparatus is adapted to engage with a placement apparatus.

The intracorporeal apparatuses are designed to both physically engage the placement apparatus, and respond to energy from an extracorporeal apparatus. A preferred embodiment accomplishes this by using magnets 120 disposed in one end 104 of the intracorporeal apparatus opposite the fastener end 414. To aid in engaging a placement apparatus, the magnet attracts an end of the placement apparatus containing a material attracted to the magnet. When the end of the placement apparatus is drawn near the end of the intracorporeal apparatus containing the magnet, the two apparatuses are attracted. If there is no impeding material located between the placement and intracorporeal apparatuses, the two apparatuses will contact and stick to each other, end to end. Advantageously, the magnetic end 104 of the intracorporeal apparatus is rounded to align axially with the placement apparatus. This alignment is imperative to allow the surgeon to retract both the placement and intracorporeal apparatuses through the trocar as well as to allow the interfaces of the placement apparatus to correctly engage the mating nodes of the intracorporeal apparatus. To further aid engaging and aligning the intracorporeal apparatus to the placement apparatus, grooves or ridges 108 are placed on the end 104 of the intracorporeal apparatus to match the grooves or ridges 108 placed on the end of the placement apparatus. When the two apparatuses are pulled proximate to each other by their magnetic attraction, the grooves and ridges force the two apparatuses to align with the end of the placement apparatus slightly overlapping the end of the intracorporeal apparatus, and forming a tight connection.

Figure 2B:
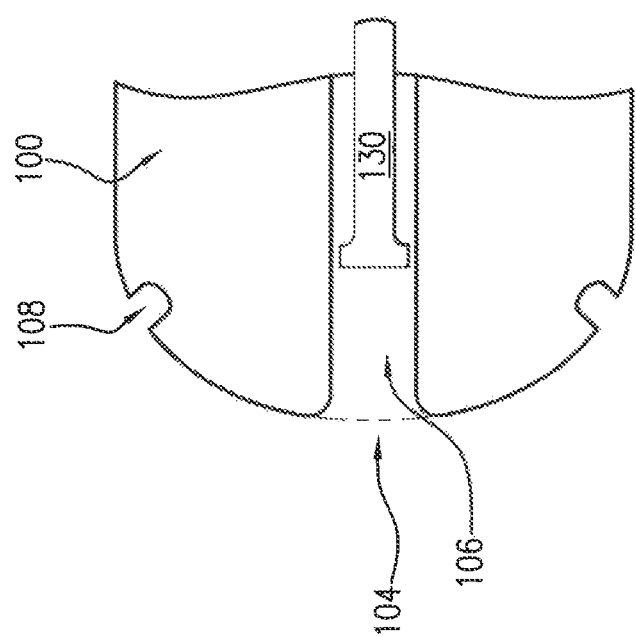
FIG. 2B is an embodiment of a magnetically responsive portion of an intracorporeal apparatus.

In a similar alternative embodiment shown in FIG. 2B, a portion of the body 100 of the intracorporeal apparatus is made of a material responsive to magnetic energy, and the magnet is instead disposed in the end of the placement apparatus. With this embodiment, the magnet on the placement apparatus may be a permanent magnet or an electromagnet. The function performed by this reversed embodiment is identical to the function as described above.

As with all medical devices, sterilization is a key consideration. Typically, sterilization of medical equipment is performed using an autoclave, which amongst other things, heats the equipment to a temperature higher than any germ can withstand to kill any germs present. Unfortunately, some embodiments of the present invention utilize permanent magnets, which when heated near a certain temperature known as the Curie temperature, will permanently lose their magnetism. Therefore, special consideration in design and use must be made to ensure that the tools are both sterile and properly magnetized. The simplest procedure to ensure correct magnetization is to use a new device with a fresh magnet for each surgery. Alternatively, magnets may be employed having Curie temperatures well in excess of sterilization temperatures. Other embodiments of the invention are designed to accommodate reuse.

Figure 2C:
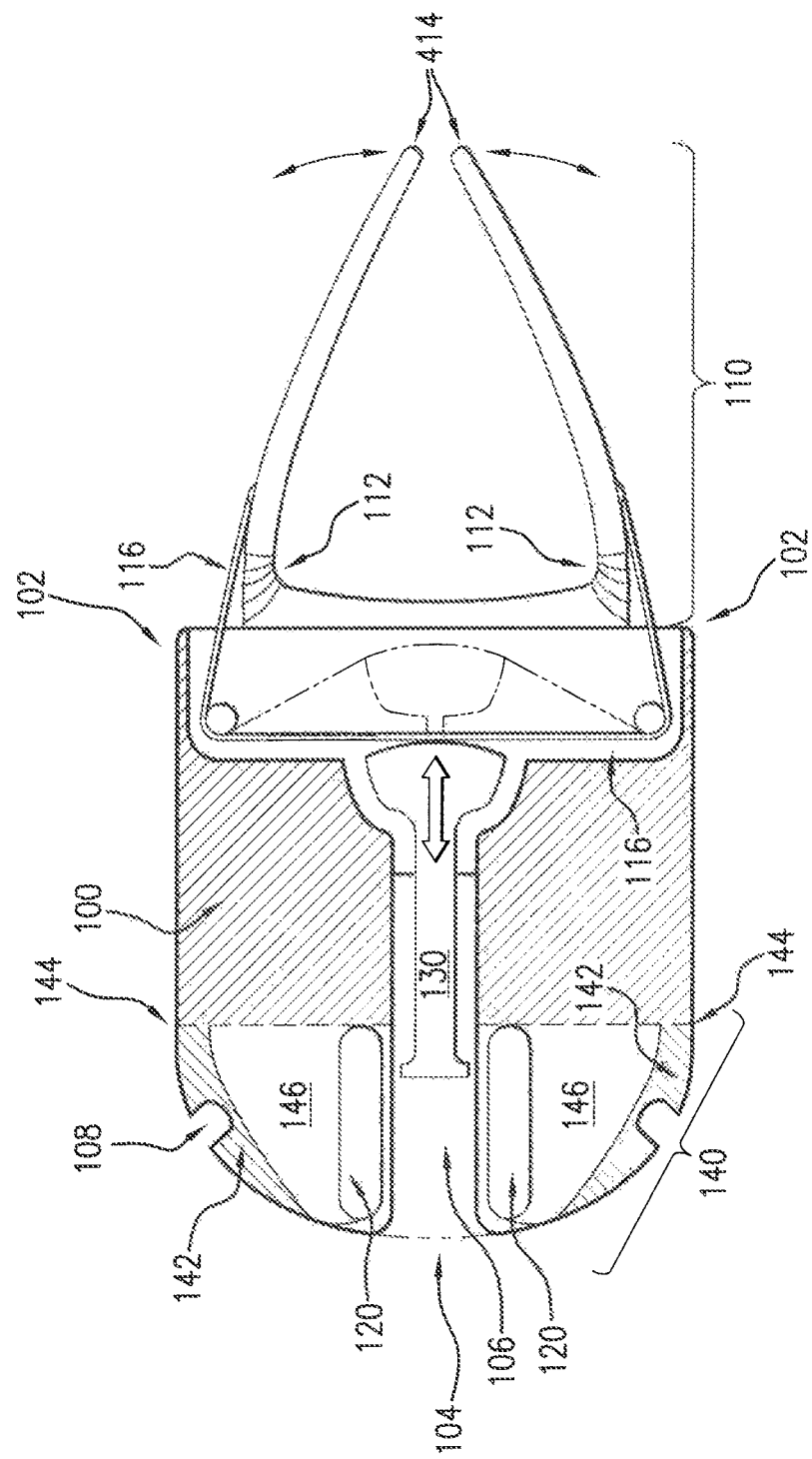
FIG. 2C is an embodiment of an intracorporeal apparatus, wherein the design provides for reuse of magnetic material.

One such embodiment of the intracorporeal apparatus is shown in FIG. 2C and is designed to permit reusing the magnet, but allowing the choice of disposing the rest. In this embodiment, the body 100 is at least partially covered by a sterile plastic shell. The body 100 has a resealable chamber 140 proximate the end 104 which engages the placement apparatus, wherein the permanent magnet 120 is placed. In the preferred embodiment, the chamber is formed by a cap 142 over a hollows 146 in the body wherein the cap screws or presses into the rim 144 of the hollows. After a surgery, the surgical team can remove the magnet 120 from the intracorporeal apparatus, and determine whether to sterilize the rest of the apparatus or discard it. If the team chooses to sterilize its used intracorporeal apparatuses, after sterilization, the team may place an available magnet back into the resealable chamber 140 of the now sterile apparatus. The team may also choose to use an unused sterile intracorporeal apparatus, in which case they may place an available magnet into its resealable chamber 140 and reseal the chamber, preparing it for surgery. In either method, the magnet is removed after surgery, and thus never exposed to the destructive heat of an autoclave.

Another embodiment of the intracorporeal apparatus is designed around reusing the entire apparatus. In this embodiment, the body 100 is made of a magnetically inert metal. Like the previous embodiment, the body of the intracorporeal apparatus has a resealable chamber 140 proximate the end 104 to house a permanent magnet. Similarly, in the preferred embodiment, the resealable chamber 140 is formed by a metal 142 cap over a hollows 146 in the body wherein the cap screws or presses into the rim 144 of the hollows 146. After a surgery, the surgical team can remove the magnet 120 from the intracorporeal apparatus, and then sterilize this embodiment of the apparatus in an autoclave. To prepare for a surgery, the surgical team may use either an unused intracorporeal apparatus or an intracorporeal apparatus that has been autoclaved, perfecting preparation for surgery by placing an available magnet into the resealable chamber 140 and resealing the chamber. Using this embodiment and method, because the magnet was removed after surgery, it is never exposed to the destructive heat of an autoclave.

Known methods of sterilization not involving heating may, of course, be conveniently employed to sterilize the apparatus of the invention.

This structure forms the platform for nearly limitless types of attachments and fasteners to be constructed for the surgeon's use. Such conceived attachments include screws, loops, clips, clamps, and the like. A screw may be useful for piercing and driving into a thick or muscular organ, such as a uterus, to gain appropriate traction to operate. The screw embodiment of the intracorporeal apparatus shown in FIG. 2D may have a port 106 on its end 104 to receive a type of energy and convert it into rotational energy. The surgeon using this embodiment may use the rotation of the screw 210 to drive the intracorporeal apparatus into the tissue which it is desired to manipulate.

In a preferred embodiment of the screw intracorporeal apparatus, a matching placement apparatus 3 has an interface such as a rotatable knob 220 on the portion of the placement apparatus that remains outside the patient's body. Twisting the knob 220 manipulates a shaft 230 which connects to a node 240 at the end of the placement apparatus. This node engages a second mating node 250 on the screw intracorporeal apparatus. The second node 250 is in turn mechanically connected to the screw 210 by an axle 260, which is adapted to rotate independently from the body 100. Therefore, twisting the knob 220 on the placement apparatus rotates the screw 210 on the intracorporeal apparatus. The length of the screw 210 may be varied in order to obtain the optimal distance between the body part which it is desired to manipulate and the abdominal wall. Another embodiment includes a non-human powered drive in the placement apparatus to drive the shaft 230 and cause the screw 210 to rotate at a higher power than a human can exert without strain.

Figure 2E:
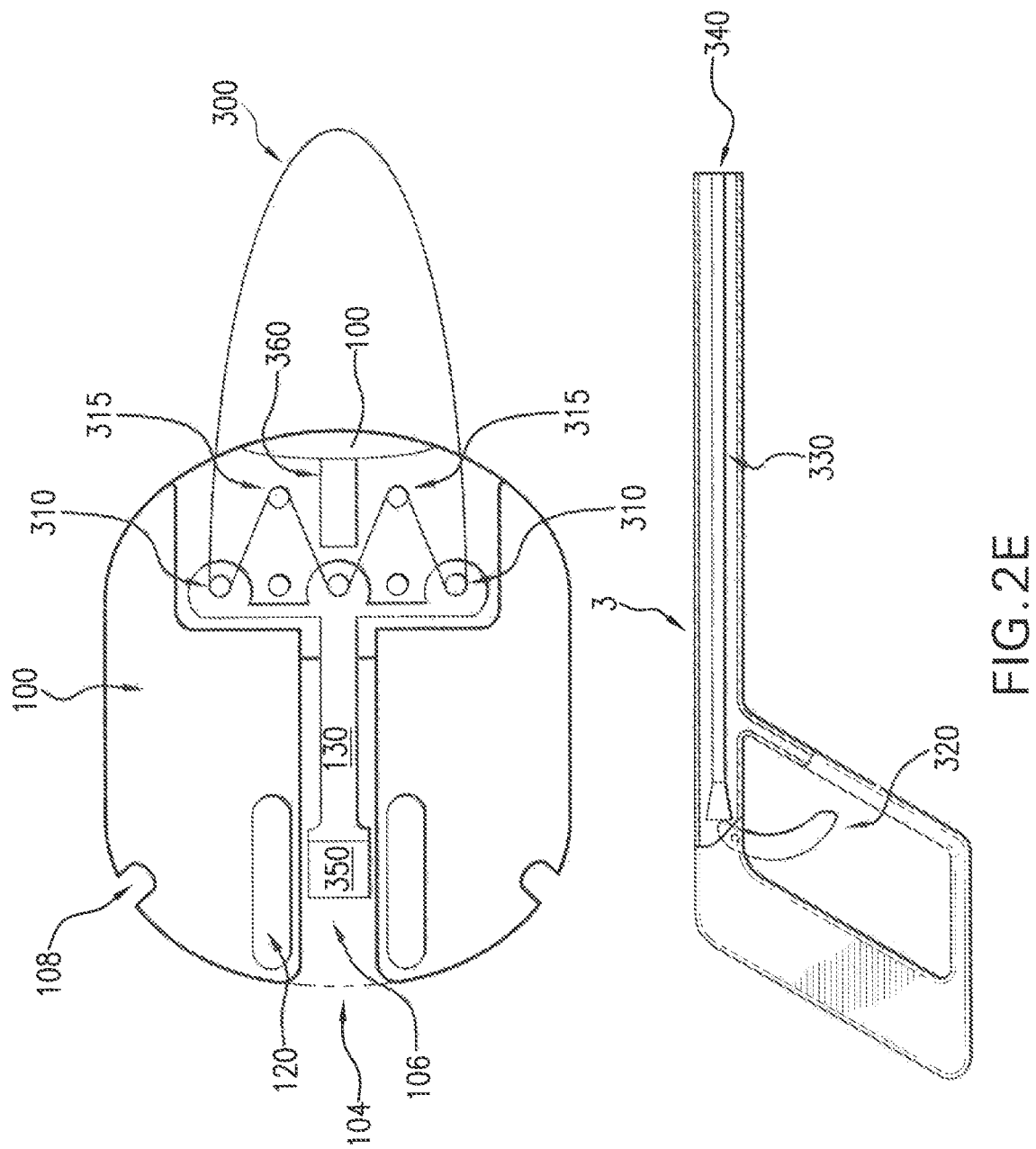
FIG. 2E is alternative embodiment of an intracorporeal apparatus with a loop mechanism for placement of objects.
Figure 2F:
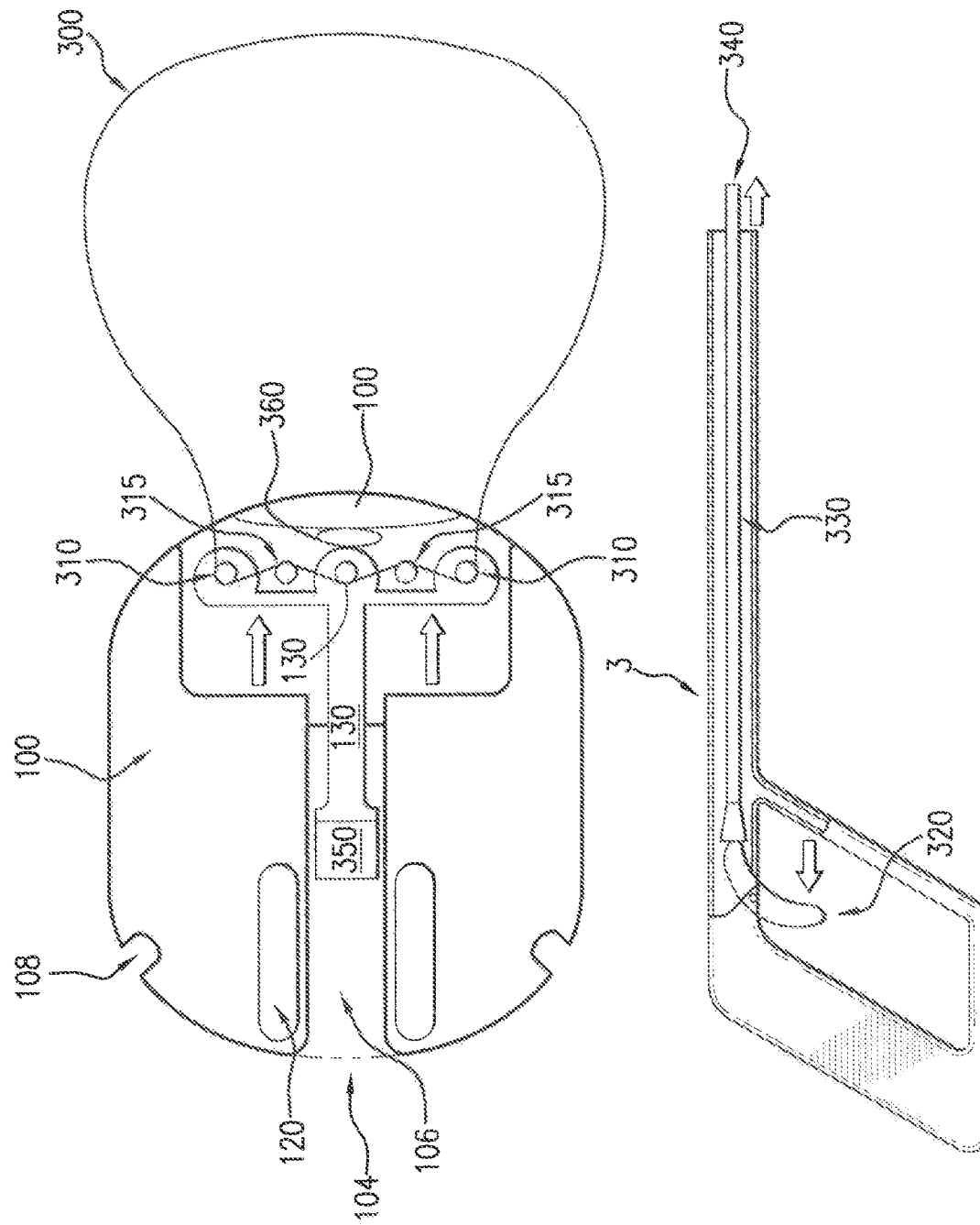
FIG. 2F is an alternative embodiment of an intracorporeal with a large loop mechanism.

Another embodiment of an intracorporeal apparatus, shown in FIGS. 2E and 2F is in the form of a loop. The loop embodiment may be used to attach to an object by placing the loop around the object, tightening the loop and capturing the object. The loop can later be loosened to release the object when finished.

In a preferred embodiment of the loop intracorporeal apparatus, a matching placement apparatus 3 has an interface such as a lever, button, or trigger 320 on the portion of the body that remains outside the patient's body. This trigger 320 drives a shaft 330 which connects to a node 340 at the first end of the body. This node engages a second mating node 350 on the loop intracorporeal apparatus. This node 350 is in turn mechanically connected to one or both ends of the loop 300 such that as the node 350 moves towards the loop, the loop opens, and as the node moves away from the loop, the loop closes. Therefore, the loop opens and closes in response to the surgeon moving the trigger 320 on the placement apparatus outside the patient's body.

An additional feature is a locking mechanism which maintains the tightened loop when the intracorporeal apparatus is not engaged with a placement apparatus. The mating node 350 on the intracorporeal apparatus is tensioned with a spring 360. This spring pushes the mating node away from the loop, thus holding the loop closed. However, when engaged with a placement apparatus, the surgeon's pressure on the trigger 320 can easily overcome the spring, forcing the loop to open.

Inside the intracorporeal apparatus, the loop 300 is actuated by moving pulleys 310 and stationary pulleys 315. Moving pulleys 310 are mounted on a piston 130. The loop 300 is threaded between moving pulleys 310 and stationary pulleys 315 as shown in FIG. 2E. When the mating node 350 is pushed towards the loop, piston 130 and moving pulleys 310 advance toward the stationary pulleys 315. As shown in FIG. 2F, this shortens the internal path loop 300 must take within body 100, allowing more of the loop to extend outside body 100. When the mating node 350 is pushed towards the end 104, piston 130 and moving pulleys 310 return back to their extended position as shown in FIG. 2E. As shown in FIG. 2E, this lengthens the internal path loop 300 must take within body 100, causing less of the loop to extend outside the body 100. When force is removed from mating node 350, spring 360 causes piston 130 and mating pulleys 310 to return to this long-path state.

A third embodiment of the intracorporeal apparatus is a clip mechanism. The clip embodiment can be used to attach a surgical clip to an object proximate the end of the clip intracorporeal apparatus while retracting the object, and leaving the clip in place. In a preferred embodiment of the clip intracorporeal apparatus, a matching placement apparatus has an interface such as a lever, button, trigger on the portion of the apparatus that remains outside the patient's body. This trigger drives a shaft which connects to a node at the end of the apparatus. This node engages a second mating node on the clip intracorporeal apparatus. The second node is in turn mechanically connected by a piston 130 such that as the node moves toward the clip, the clip is expelled from the clip intracorporeal apparatus and closes permanently on the object. Therefore, the clip is closed about an object in response to the surgeon moving the trigger on the placement apparatus outside the patient's body.

Figure 5:
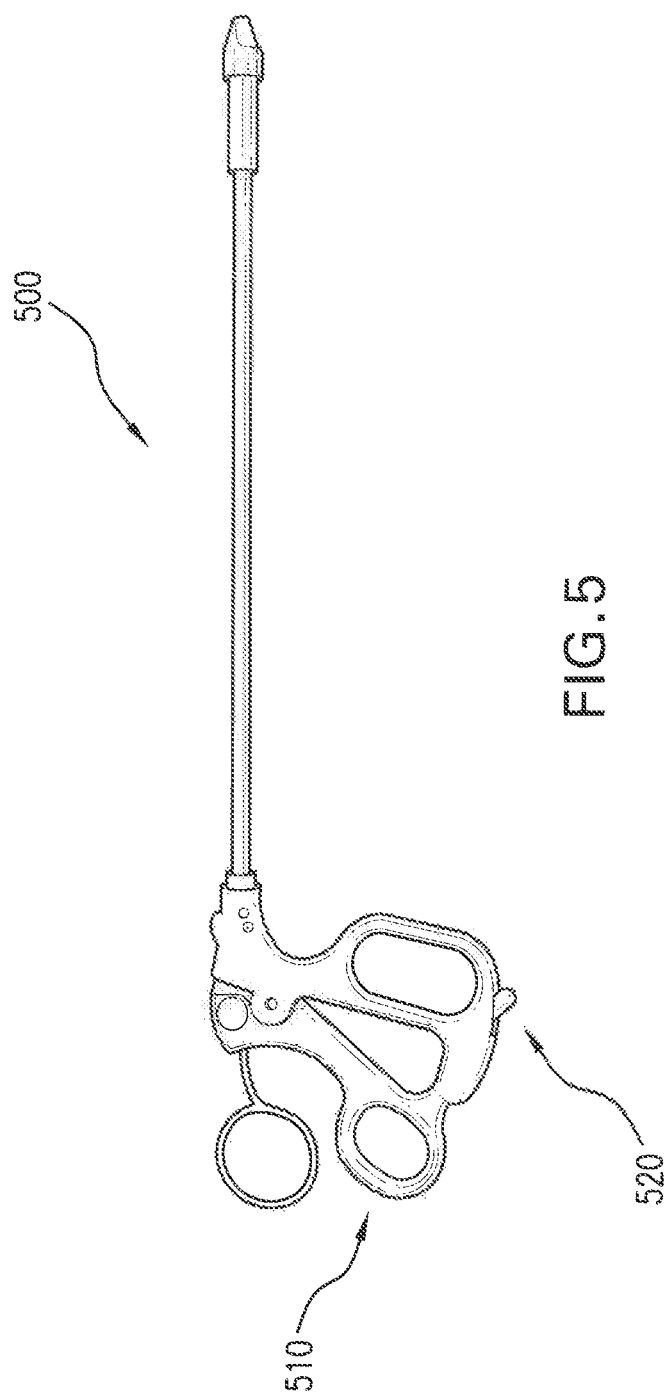
FIG. 5 is an alternative embodiment of an intracorporeal and placement apparatuses.

In an alternative embodiment shown in FIG. 5, the placement apparatus 500 may have an interface in the form of a scissor-like mechanism 510. An additional feature is a locking mechanism 520 that maintains the placement apparatus' lever, button, trigger, or scissor-like mechanism in a position set by the user. The locking mechanism 510 prevents the shaft from moving once the user supplied force has positioned the shaft. This allows the surgeon to maintain an intracorporeal apparatus engaged with a placement apparatus in a position when trying to attach the intracorporeal apparatus to a patient's body.

A fourth embodiment of the intracorporeal apparatus is a clamp. The clamp embodiment can be used to form a simple attachment to an object whereby the surgeon opens the clamp and closes it around an object, to maintain its position. The clamp can later be opened to release the object.

In a preferred embodiment of the clamp intracorporeal apparatus, shown in FIG. 2A, a matching placement apparatus 3 has an interface such as a lever, button, or trigger 420 on the portion of the apparatus that remains outside the patient's body. This trigger 420 manipulates a shaft 430 which connects to a node 440 at the end of the apparatus. This node 440 engages a second mating node 450 on the clamp intracorporeal apparatus. The second node 450 is in turn mechanically connected by a piston 130 to one or both sides of the clamp 410 such that as the node 450 moves towards the clamp, the clamp opens, and as the node moves away from the clamp, the clamp closes. Therefore, the clamp opens and closes in response to the surgeon moving the trigger 420 on the placement apparatus outside the patient's body. An additional feature is the locking mechanism which holds the clamp tight when the intracorporeal apparatus is not engaged with a placement apparatus. The mating node 450 on the intracorporeal apparatus is spring tensioned by use of the clamp 410. The clamp is preferably constructed of a single rigid material that when at rest will close down its tines 414 to a point. For additional grip, the teeth 418 may be disposed near the end of one or both tines 414. The tines are connected to each other by a flexible filament 416 which is thread through the body 100 across pulleys 418. The piston 130 is in physical contact with the filament 416 inside the body 100. The spring function of the tines 414 keeps the filament 416 in a taut position. This taut filament 416 pushes against the piston 130 away from the clamp. However, when engaged with a placement apparatus, the surgeon's pressure on trigger 420 can easily overcome the tension placed on the filaments by the tines 414. This pressure forces mating node 450 and piston 130 to move towards the clamp 410, stretching filament 416. As pressure is applied to the filament 416, the tines 414 are forced to open.

Figure 3A:
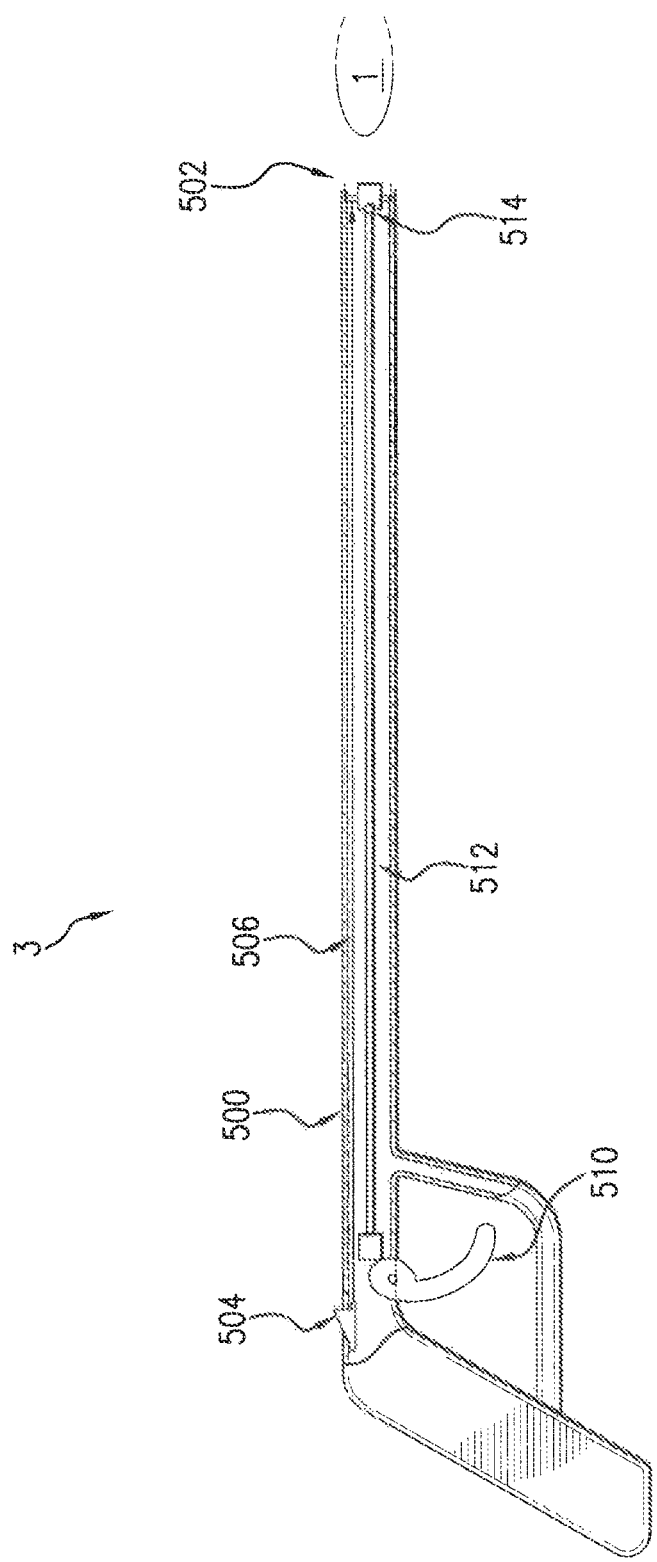
FIG. 3A is a detailed embodiment of a placement apparatus.
Figure 3B:
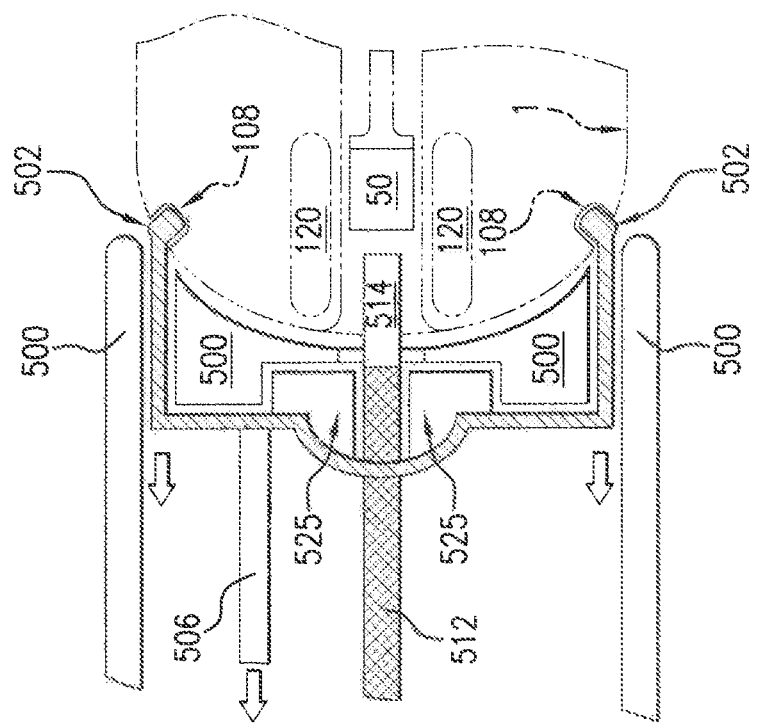
FIG. 3B is an embodiment of a placement apparatus engaging an intracorporeal apparatus.

The placement apparatuses are the tools that are used to physically position the intracorporeal apparatuses inside the patient's body and cause them to attach to objects. The preferred embodiment, shown in FIGS. 3A and 3B, comprises a body 500 having some shape with some length at least in one cross section having a size no greater than a trocar being of a length which would allow it to access distant areas within the body and allow the surgeon to comfortably operate the portion of the apparatus remaining outside the patient's body.

The preferred embodiment further comprises a connector 502 disposed on the end of the body that is placed through the trocar into the patient's body. This connector is adapted to engage and disengage any of numerous intracorporeal apparatuses 1. The connector is controlled by an engagement interface near the end of the body that remains outside the body during surgery. This engagement interface can be a button, an electrical connection to an external device or, most preferably, an engagement lever 504 that slides in the direction along the body's length, and is mechanically attached by a shaft 506 to the connector 502 at the far end of the body 500. When the engagement lever 504 is moved closer to the far end, the connector 502 moves with the engagement lever to capture and engage with an intracorporeal apparatus 1. When the lever is moved away from the far end, the connector moves with the lever to disengage and release an intracorporeal apparatus.

The preferred embodiment also comprises another interface near the end of the body that remains outside of the patient's body. This action interface transmits mechanical energy from the surgeon or another source outside the body to an intracorporeal apparatus if engaged to the placement apparatus. The preferred embodiment for the action interface is a lever in the form of a trigger 510 which is spring loaded. The trigger 510 is mechanically connected to a node 514 at the far end of the body 500 by a shaft 512. This node 514 engages with a mating node 50 on an intracorporeal apparatus 1, the intracorporeal apparatus then in turn converts the delivered energy for its uses. The action interface may also be alternatively an electrical connection to an external device.

In order to assist engaging with the preferred embodiment of the intracorporeal apparatus described above, the placement apparatus must have some magnetically responsive material to attract the permanent magnet in the intracorporeal apparatus. The preferred embodiment thus has a mass of magnetically responsive material 525 disposed within the body 500 of the placement apparatus near the end that enters the patient's body. This magnetically responsive material 525 is mechanically connected to the connector 502 and moves toward the end when the engagement interface is moved towards the end. The magnetically responsive material 525 moves away from the end further up the body 500 when the engagement interface is moved away from the end. As a result, when the engagement interface is positioned to engage an intracorporeal apparatus, the magnetically responsive material is most proximate the end of the body, and thus more easily attracted to the magnet in the intracorporeal apparatus. Furthermore, when the engagement interface is positioned to disengage from the intracorporeal apparatus, the magnetically responsive material is pulled away and outside the attractive reach of the intracorporeal apparatus magnet, thus allowing the two apparatuses to separate.

It will be appreciated that any magnetically responsive material may be utilized in accordance with the teaching of the invention. Presently preferred magnetically responsive material includes ferrous or iron-containing material, rare-earth containing materials, and the like. Exemplary magnetic materials are listed in Table 1.

Figure 3C:
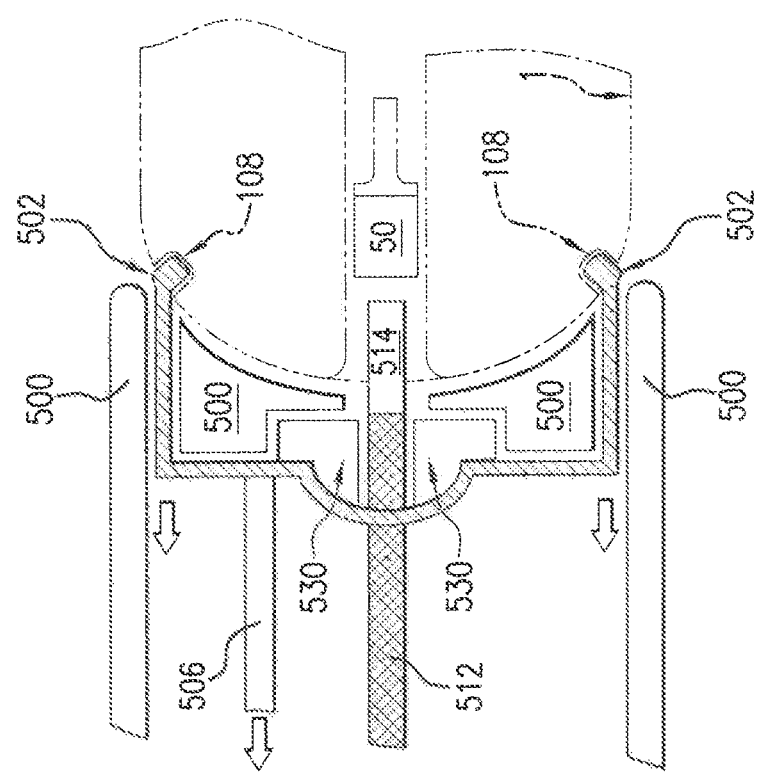
FIG. 3C is an alternative embodiment of a placement apparatus utilizing magnetic energy.
Figure 3D:
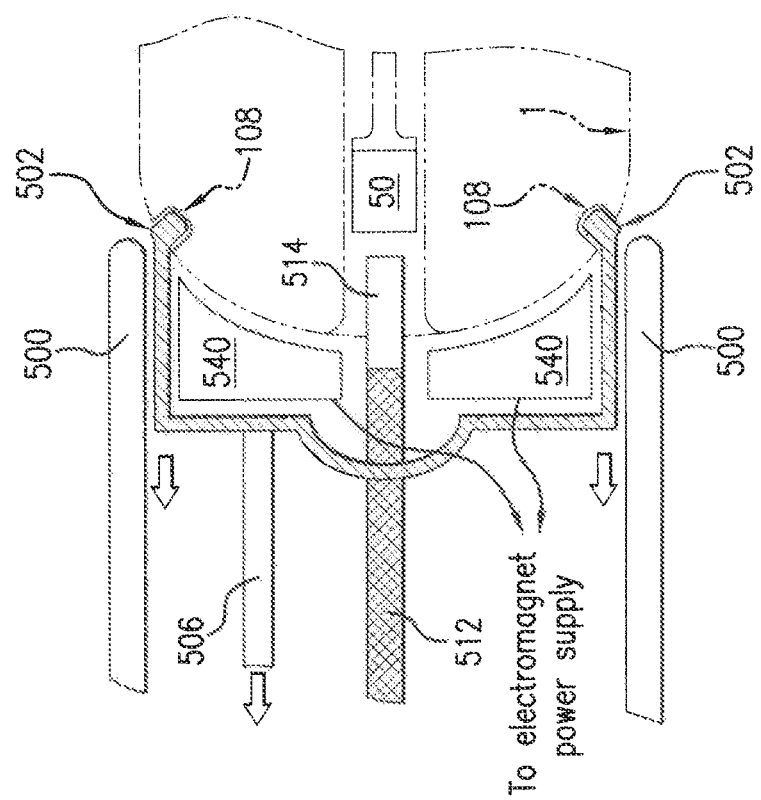
FIG. 3D is an alternative embodiment of a placement apparatus utilizing electromagnetic energy.
Figure 3E:
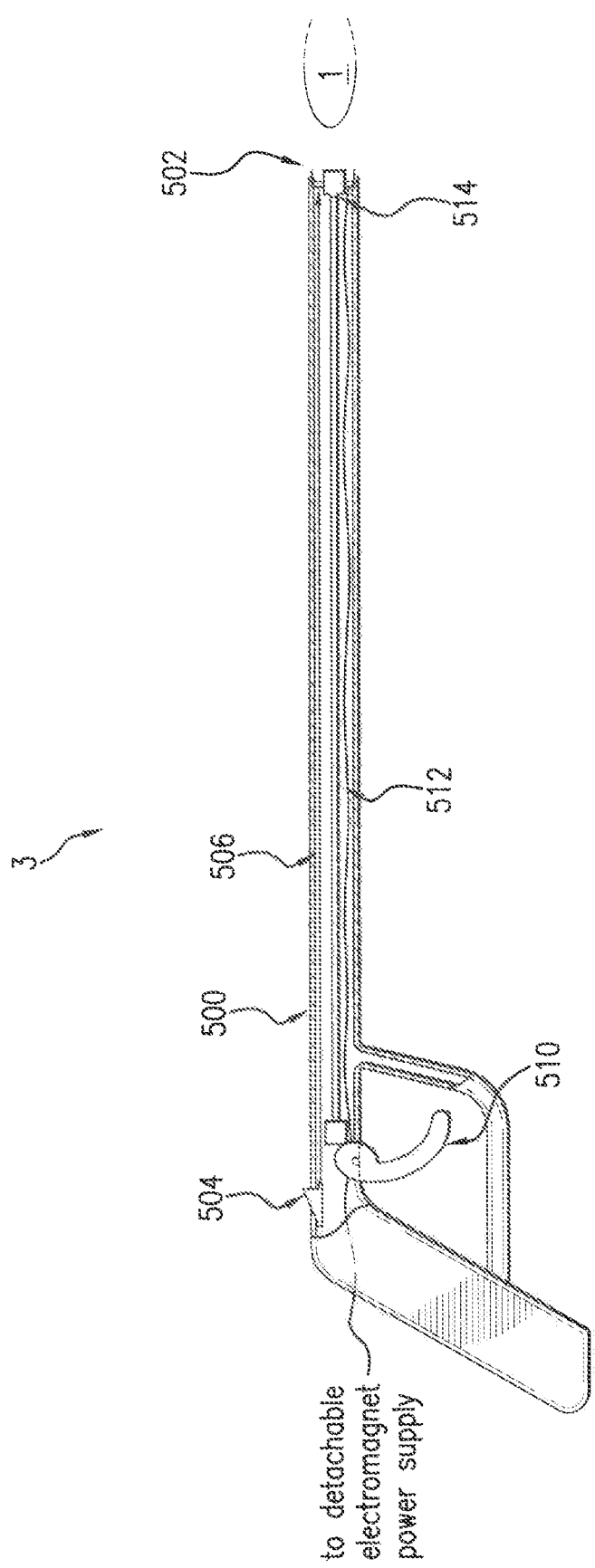
FIG. 3E is an alternative embodiment of a placement apparatus attached to an electromagnetic energy source.
Figure 3F:
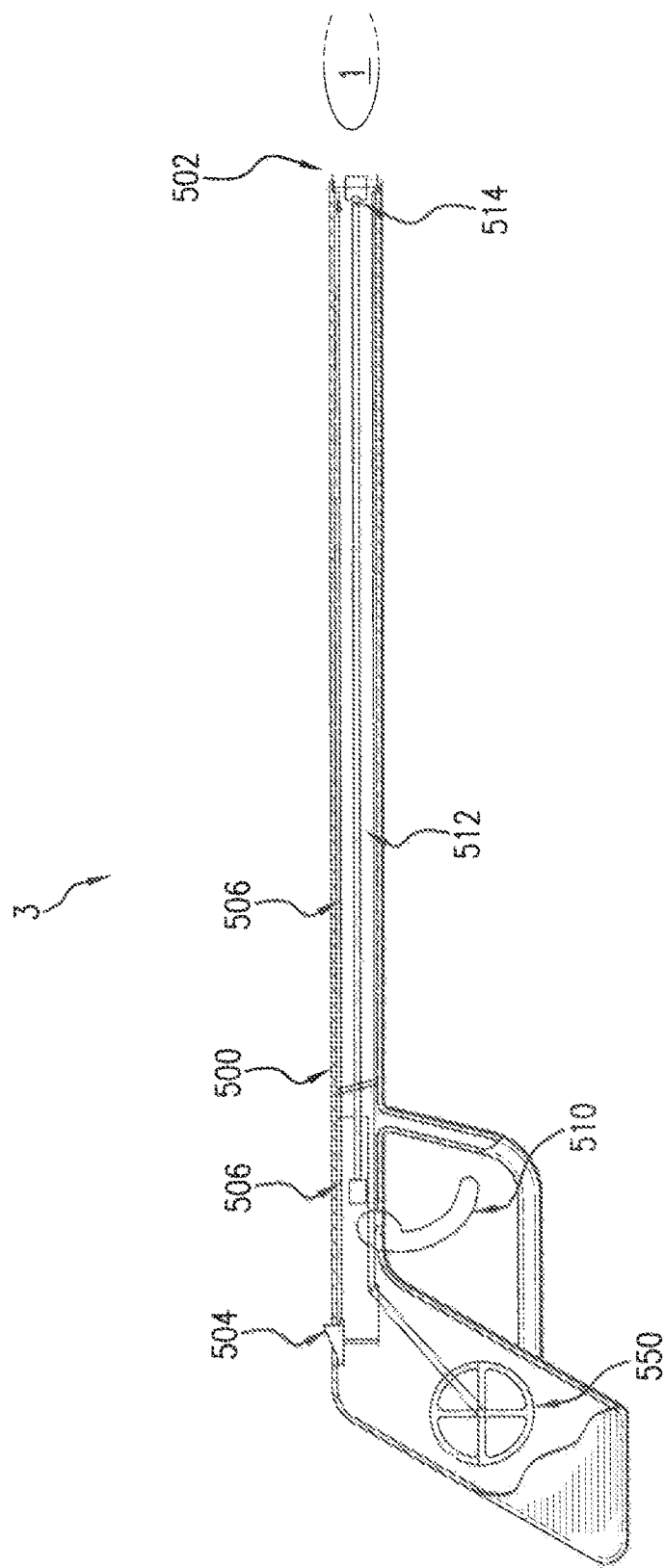
FIG. 3F is an alternative embodiment of a placement apparatus with an interface to generate rotational energy.

In another embodiment, shown in FIGS. 3C and 3D, the placement apparatus contains a magnet 530 or electromagnet 540 disposed near the end of the body that enters the patient's body. The magnet 530 attracts the magnetically responsive material in certain embodiments of the intracorporeal apparatuses, performing the same function in aiding the surgeon to engage the intracorporeal apparatus inside the patient's body. Similarly to the preferred embodiment, this magnet 530 may be disposed within the shaft of the body 500 and mechanically connected to the connector 502. In this way, the magnet 530 moves closer to the end of the body 500 when the engagement interface is slid towards the end. With the magnet closer to the end, the placement apparatus will more easily attract the intracorporeal apparatus. Similarly, the magnet moves into the interior of the body and further from the end as the engagement interface is slid away from the end. With the magnet further from the end, the intracorporeal apparatus will be less attracted to the placement apparatus, which will cause an easy separation.

In the case of using an electromagnet 540, the system can take advantage of controlled temporary magnetism. To engage an intracorporeal apparatus 1, the electromagnet 540 is turned on, and so attracts the magnetically responsive material 120 in a corresponding intracorporeal apparatus. Similarly, to disengage the intracorporeal apparatus, the electromagnet 540 is turned off. With slight movement from the surgeon, the intracorporeal apparatus will no longer be attracted to the placement apparatus, and the two apparatuses may be separated. To power the electromagnet, a detachable power supply connects to the placement apparatus near the end that remains outside the patient's body. This power supply being external to the placement apparatus allows the placement apparatus to be made smaller. Furthermore, because it is detachable, the surgical team may detach the power supply and sterilize the placement apparatus in an autoclave as they normally would. When sterile, the team may then reattach the power supply for use in a subsequent procedure.

A preferred embodiment also comprises a third interface near the end of the body that remains outside of the patient's body. The interface 550 when activated by the surgeon causes the connector 502 and any object engaged to it to rotate about the axis of the placement apparatus. Utilizing this embodiment, the surgeon's interface 550 may articulate an intracorporeal apparatus 1 attached to the placement apparatus in a fashion similar to the manner in which surgeons currently rotate laparoscopic instruments within a patient's body.

Figure 3G:
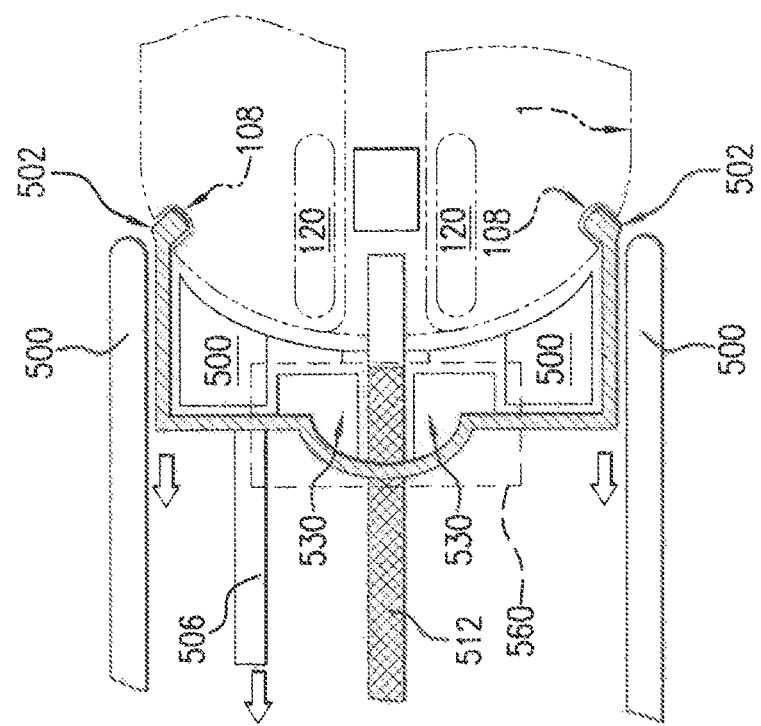
FIG. 3G is an alternative embodiment of a placement apparatus, wherein permanent magnets used in the device may be placed in a resealable chamber.

In embodiments of the placement apparatus containing their own permanent magnets, a similar situation arises as seen in the intracorporeal apparatuses above involving sterilization. Typical sterilization in an autoclave may strip the permanent magnets of their magnetism. To prevent this in embodiments with permanent magnets, such as shown in FIG. 3G, the magnet 530 may be placed in a resealable chamber 560 proximate the end of the body 500 that is passed into the patient's body. In a preferred embodiment, the resealable chamber is formed by a cap 562 over a hollow in the body wherein the cap presses into the rim of the hollows. After a surgery, the surgical team can remove the magnet 530 from the placement apparatus, and sterilize the remainder in an autoclave. In preparation for a subsequent surgery, the team may take an unused or an autoclaved placement apparatus, place an available magnet into its resealable chamber, and replace the cap on the chamber, thereby rendering the placement apparatus ready for utilization in a subsequent surgery.

Figure 3H:
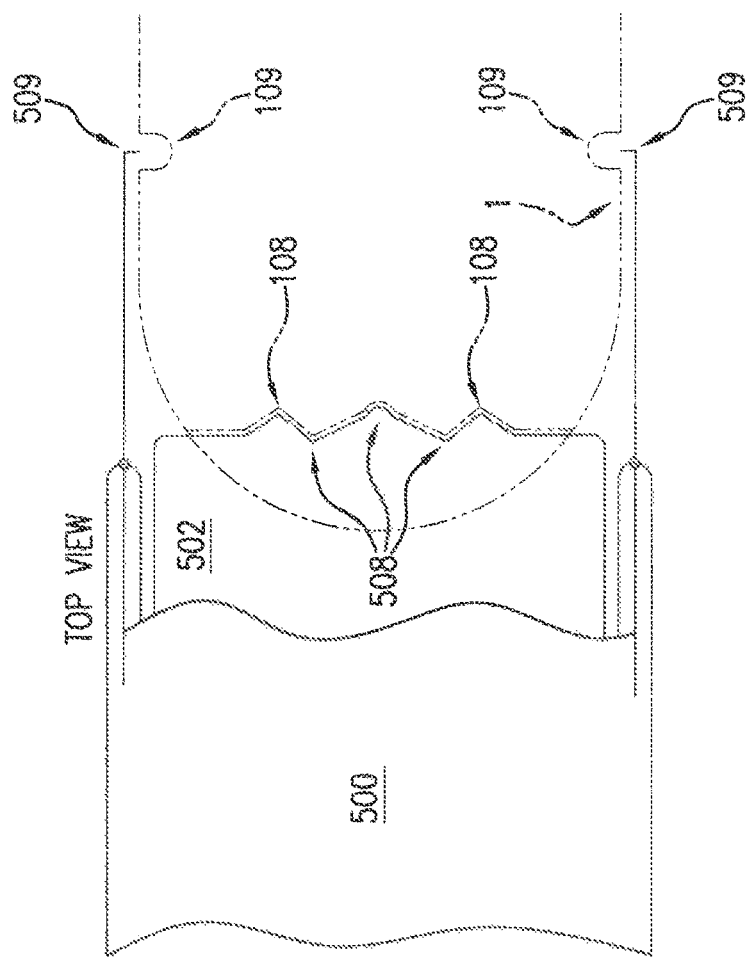
FIG. 3H is a topical view of a connector engaged with an intracorporeal apparatus.

FIG. 3H demonstrates a top view of the connector and its interaction with the intracorporeal apparatus. To further aid the engagement and alignment of the intracorporeal apparatus to the placement apparatus, grooves or ridges 108 are placed on the end of the intracorporeal apparatus to match grooves or ridges 508 on the connector 502. When the two apparatuses are pulled proximate to each other by their magnetic attraction, the grooves and/or ridges 108 force the intracorporeal apparatus to align with the grooves and ridges 508 on the connector 502 slightly overlapping the end of the intracorporeal apparatus, and forming a tight connection. Additionally, the placement apparatus may be fitted with a moveable or flexible tab 509 mechanically connected to the engagement interface. This tab 509 is adapted to fit within a groove 109 on an intracorporeal apparatus in a mating fashion when the engagement interface is moved toward the end of the body. Thus, the tab thus locks the intracorporeal apparatus to the placement apparatus.

A third major component of this system is the extracorporeal apparatus. This apparatus may be used to position an intracorporeal apparatus and any object attached to it within the patient's body. Preferred embodiments of this apparatus comprise a body of some shape with an affixed handle and preferably a magnet or other source of magnetic energy. The extracorporeal apparatuses require a magnetic field source that can produce a magnetic field sufficient to manipulate objects fastened to an intracorporeal apparatus.

Figure 4A:
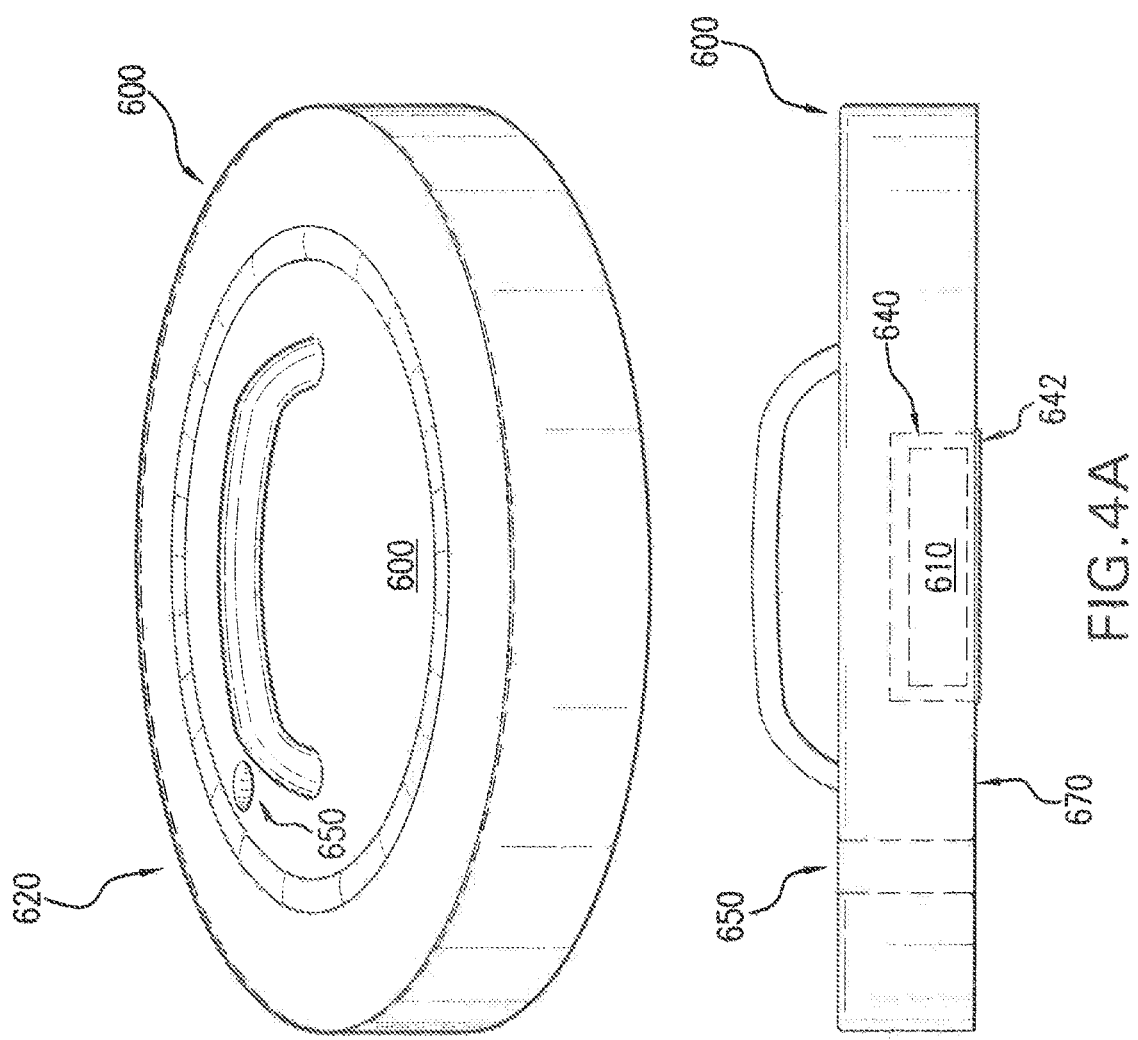
FIG. 4A is an embodiment of a magnetically energized extracorporeal apparatus.

In the preferred embodiment shown in FIG. 4A, the extracorporeal apparatus may be shaped like a disk with the magnet 610 contained in the middle of the body 600, away from the surface. In this embodiment, the body forms a shell around the magnet, comprised of either a medically inert plastic or a magnetically inert metal or a combination of both materials. Both materials are suitable to prevent the magnet from coming in direct contact with the patient's body, but also serve the purpose of protecting the magnet. Many types of magnets used in the preferred embodiments are so fragile or brittle, that their own attraction to another magnet can cause the magnet to disintegrate upon contact. In order to preserve the magnet within, the body surrounding the magnet absorbs some of the energy in the event of an impact with a hard surface or a corresponding magnaretractor apparatus.

For sterilization purposes, the extracorporeal apparatus may be partially wrapped by a disposable or sterilizable cover 620. As with the placement and intracorporeal apparatuses, the use of permanent magnets presents a situation wherein the typical method of sterilization, i.e., use of an autoclave may destroy the magnetic properties of the magnet. After use in surgery, the surgical team may remove this cover from the extracorporeal apparatus, and either discard or sterilize it for later use. In preparation for a subsequent surgery, the team then may simply place a new or sterilized cover on an available extracorporeal apparatus. In order to ensure that the sterile cover does not separate from the extracorporeal apparatus during surgery, it is preferred that the cover comprise a form-fitting boot to frictionally adhere to the body of the extracorporeal apparatus.

An additional method to ensure the extracorporeal apparatus is sterile for a subsequent surgery is to use an extracorporeal apparatus embodiment having a resealable magnet chamber. In this embodiment, the resealable chamber 640 resides in the central area of the apparatus body 600. In the preferred embodiment, the chamber is formed by a cap 642 over a hollows in the body wherein the cap screws or presses into the rim of the hollows. After a surgery, the surgical team can remove the magnet 610 from the extracorporeal apparatus 2, and determine whether to sterilize the apparatus or discard it. If the team chooses to sterilize its used extracorporeal apparatuses, after sterilization, the team may place an available magnet back into the resealable chamber 640 of the now sterile apparatus. The team may also choose to use an unused sterile extracorporeal apparatus, in which case they may place an available magnet into its resealable chamber in preparation for surgery. In either method, the magnet is never exposed to the destructive heat of an autoclave.

In all of the above embodiments including a permanent magnet, there are many choices of magnets available with varying benefits and detriments to each of their respective uses. The magnets of the extracorporeal apparatuses must be strong enough to exert sufficient pulling (or pushing) force to permit manipulation of the desired object within the body cavity from a distance of several centimeters. For example, in performing a hysterectomy on a fibroid uterus, the magnet pulling an attached intracorporeal apparatus must reach through as much as 5 centimeters or even more of the patient's body to cause the uterus to move.

While this situation suggests the use of a larger, more powerful magnet, other considerations require the magnet to be as weak as possible without disrupting function. For instance, it is very likely that the surgeon will place more than one intracorporeal apparatus inside the patient's body. An extremely strong magnet may disadvantageously attract both the intended and an unintended intracorporeal apparatus, as well as any other objects containing magnetically responsive material in the room. Furthermore, such a strong magnet will also be physically larger than necessary to perform the procedure, thereby rendering it too unwieldy to control or anchor. A third consideration is that a very strong magnet will apply a considerable force to an object attracted to it, which may pinch tissue between the object and the magnet, with enough force to cause damage to the patient.

Accordingly, the present invention includes a set of extracorporeal apparatuses with magnets of varying sizes, shapes and materials, or an adjustable electromagnet. The first consideration for a surgical team in choosing which type of magnets to use concerns whether they will reuse the tools, and if so, how they will sterilize them. A surgical team choosing to discard used extracorporeal apparatuses is only limited in its choice by the expense of individual magnets, and therefore needs only consider the magnetic strength required for this particular patient or procedure.

Surgical teams that choose to reuse however must consider the Curie temperature for the magnet they wish to use, and a particular sterilization method. As mentioned above, using an autoclave may destroy a magnet's magnetism. Therefore, the team has three options for reuse. The first option is to choose a magnet with a Curie temperature much higher than their autoclave can generate, such as Samarium-cobalt or Alnico magnets. With this option, the team may simply place the entire apparatus into the autoclave as they would any other equipment. For many purposes, this may be an adequate solution. However, both Samarium-cobalt and Alnico magnets are weaker than Neodymium magnets, and such strength may be necessary for patients with thick adipose tissue or in procedures that require manipulation of deeply situated or heavy objects.

The second option is to choose an extracorporeal apparatus having a removable magnet in a resealable chamber. With this option, the team removes the magnet from the apparatus after use. The apparatus then may be placed in the autoclave as the team typically would to sterilize equipment. After sterilization, the team would then place the magnet back into the apparatus prior to conducting another surgery. There is no limitation to the team placing the magnet in the same apparatus, as the magnet may be placed in any available apparatuses. This option will work well in any situation, however the surgical team must take the necessary precautions.

The final option is to use permanently positioned magnets within the apparatus. After use, the surgical team may place the entire extracorporeal apparatus into the autoclave, without regard to Curie temperatures until sterilization is achieved. Since the magnet embedded in the apparatus may have been demagnetized, before use, the team must place the apparatus into a remagnetizer to return the magnet to its full magnetic capabilities. The team may perform this on-site, or return the apparatus to an appropriate vendor who can perform a remagnetizing service to re-magnetize the magnets. A preferred embodiment of a remagnetizer includes a body which physically mates with the extracorporeal apparatus to hold it in one position during the re-magnetization process. The remagnetizer exposes the magnet within the magnaretractor apparatus to a high-intensity magnetic field, which causes the magnet to retain its original magnetic field. This option may similarly be used to sterilize and re-magnetize intracorporeal and placement apparatuses.

TABLE 1

Exemplary magnets and their characteristics

| Material | Curie Temp. | Characteristics |
| --- | --- | --- |
| Cobalt (Co) | 1115° C. | Very high Curie temp. Low strength |
| Alnico | 800° C. | High Curie temp. Much weaker than SmCo and NIB magnets Much stronger than other non-rare earth magnets |
| Iron (Fe) | 770° C. | High Curie temp. Low strength |
| Samarium-cobalt (SmCo) | 680 to 800° C. | High Curie temp. Very high strength More expensive than NIB magnets Weaker than NIB magnets Very brittle |
| Nickel (Ni) | 354° C. | Low strength Low Curie temp. |
| Neodymium (NdFeB or NIB) | 320° C. | Strongest permanent magnet currently sold commercially Less expensive than SmCo magnets Low Curie temperature Brittle but less so than SmCo Highly corrosive |

While the size and material of the magnet determines its strength, the shape has an effect on how much the magnetic field "falls off" over distance. For example, a magnet shaped like a long rod may be strong enough to cause an object weighing 1 kilogram from one centimeter away to accelerate towards the magnet. This same magnet can only cause the same acceleration on an object weighing 250 grams from two centimeters away or 40 grams from five centimeters away. In this situation, the strength of the magnetic field is said to fall off with the square of the distance, giving this magnet a deep reach. Although a magnet having a different shape may also be able to cause an object weighing 1 kilogram from one centimeter away to accelerate towards it, however, at two centimeters, it may only have the capacity to cause the same acceleration on an object weighing 125 grams, and from five centimeters the magnet may only cause the same acceleration on an object weighing 8 grams. In this situation, the strength of the magnetic field is said to fall off with the cube of the distance, i.e., a shallower reach. Thus, the surgeon will have the option of choosing an extracorporeal apparatus with a deeper or shallower reach.

During surgery, the surgeon may use special trocars with graduations to measure the thickness of the abdominal walls of the patient's body. With that measurement and the surgeon's knowledge of the approximate weight of the object to be moved, the surgeon may choose the appropriate extracorporeal apparatus having a magnet of the required strength amongst the plurality of available apparatuses.

Figure 4B:
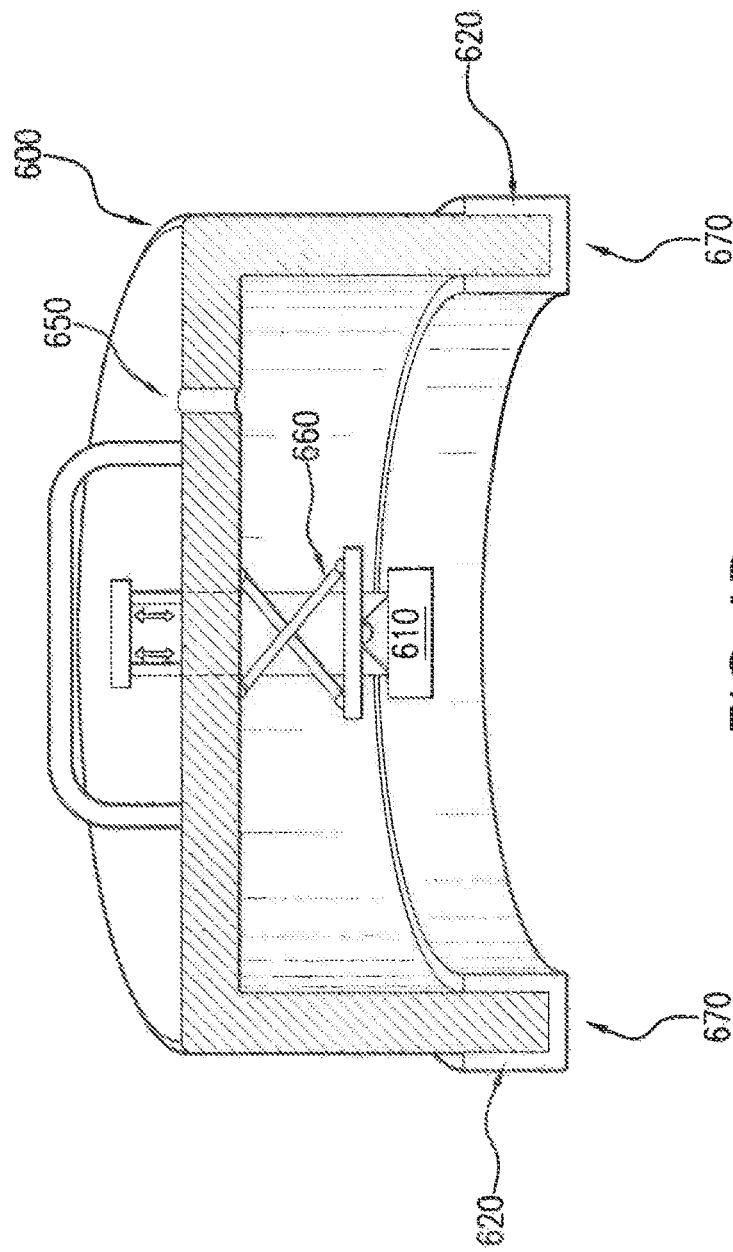
FIG. 4B is an alternative embodiment of an extracorporeal apparatus containing a movable magnet mechanism.

The extracorporeal apparatus may be fine tuned by disposing the magnet on an articulable joint. In this embodiment, preferably utilizing a cup shape as shown in FIG. 4B, the magnet 610 may be moved closer or further away from the patient's body by manipulating the articulable joint 660. This way, the surgeon may exact greater or lesser force on an object held by an intracorporeal apparatus within the body. Additionally, the surgeon may use intracorporeal apparatuses containing its own magnets, which will interact with the magnet 610 in the extracorporeal apparatus 2. Using the articulable joint 660, the surgeon may rotate the magnet of the extracorporeal apparatus 600, which would cause the magnet of the nearby intracorporeal apparatus to rotate in sympathy. The result is that the surgeon can manipulate the attitude of the object within the patient's body by articulating the magnet attached to the extracorporeal apparatus.

Figure 4C:
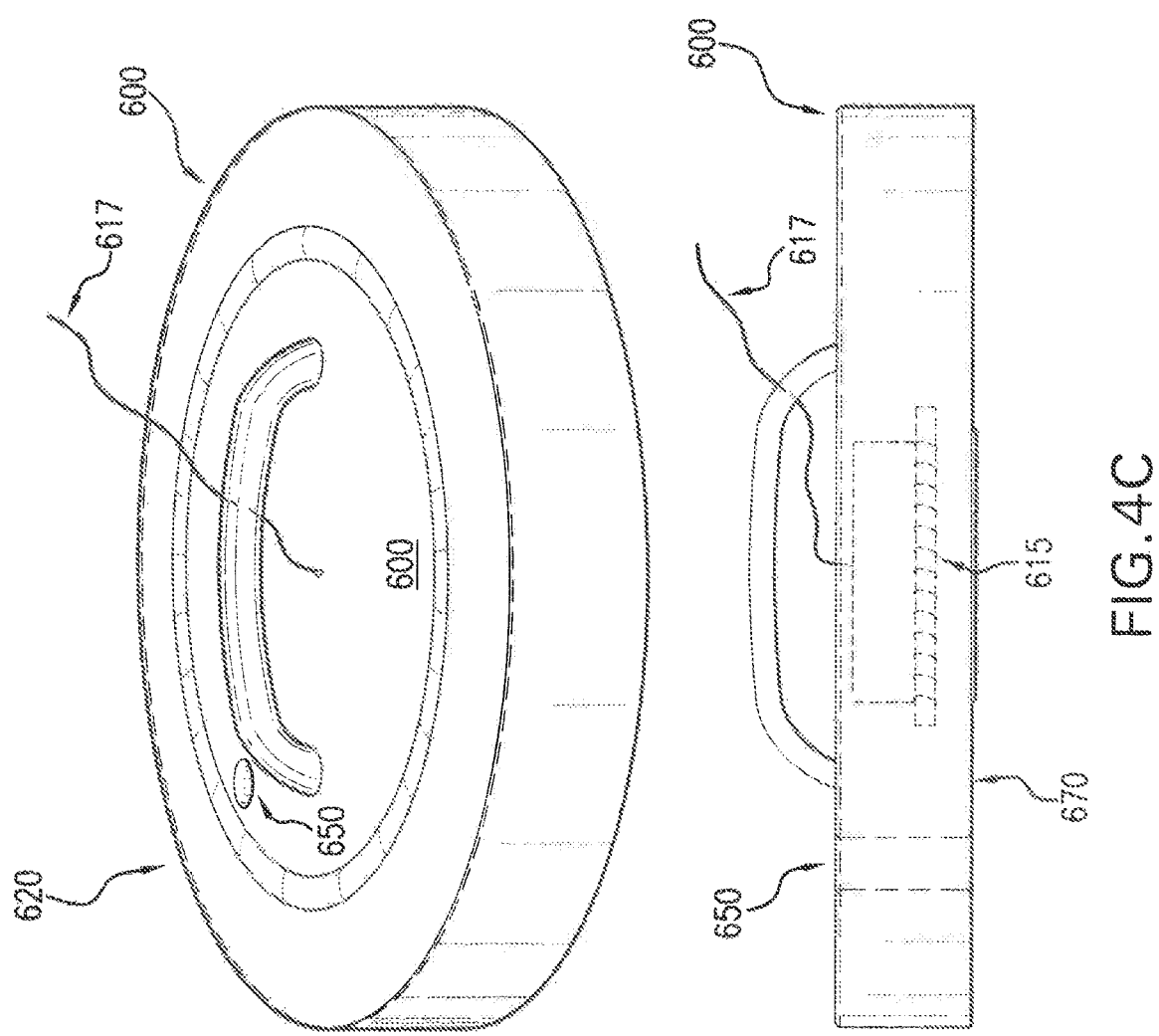
FIG. 4C is an alternative embodiment of an extracorporeal apparatus utilizing electromagnetic energy.

Another embodiment shown in FIG. 4C uses an electromagnet 615 as the source of magnetic energy. In this embodiment, the strength of the electromagnet's 615 magnetic field is adjustable to allow the surgeon to choose the smallest field required to position a single intracorporeal apparatus, and not interfere with other apparatuses or other magnetically responsive objects. A detachable power supply cable 617 provides power to the electromagnet 615.

To ease using the extracorporeal apparatus, the surgeon may lubricate the surface 670 touching the patient's body to allow it to move more easily, and anchor the apparatus to the body, the surgical drape, the surgical table, or another fixed object, to prevent the apparatus from moving once in place.

Anchoring the extracorporeal apparatus in a fixed position may also be accomplished by using an air pump. The preferred embodiments shown in FIGS. 4A, 4B and 4C dispose a port 650 on one side of the extracorporeal apparatus which may be connect to an air pump. This port allows the surgeon to position the extracorporeal apparatus 2 on the desired point on the exterior of the patient's body. Then using the air pump, the surgeon may pump air from beneath port 650, thereby decreasing the pressure between the extracorporeal apparatus 2 and the patient's body. The resulting pressure differential will gently lock the extracorporeal apparatus in position on the patient's body. When the surgeon wishes to remove the apparatus, a release valve on the air pump may be opened, allowing normal pressure to return to the region between the apparatus and the patient's body, thus unlocking the apparatus.

Figure 4D:
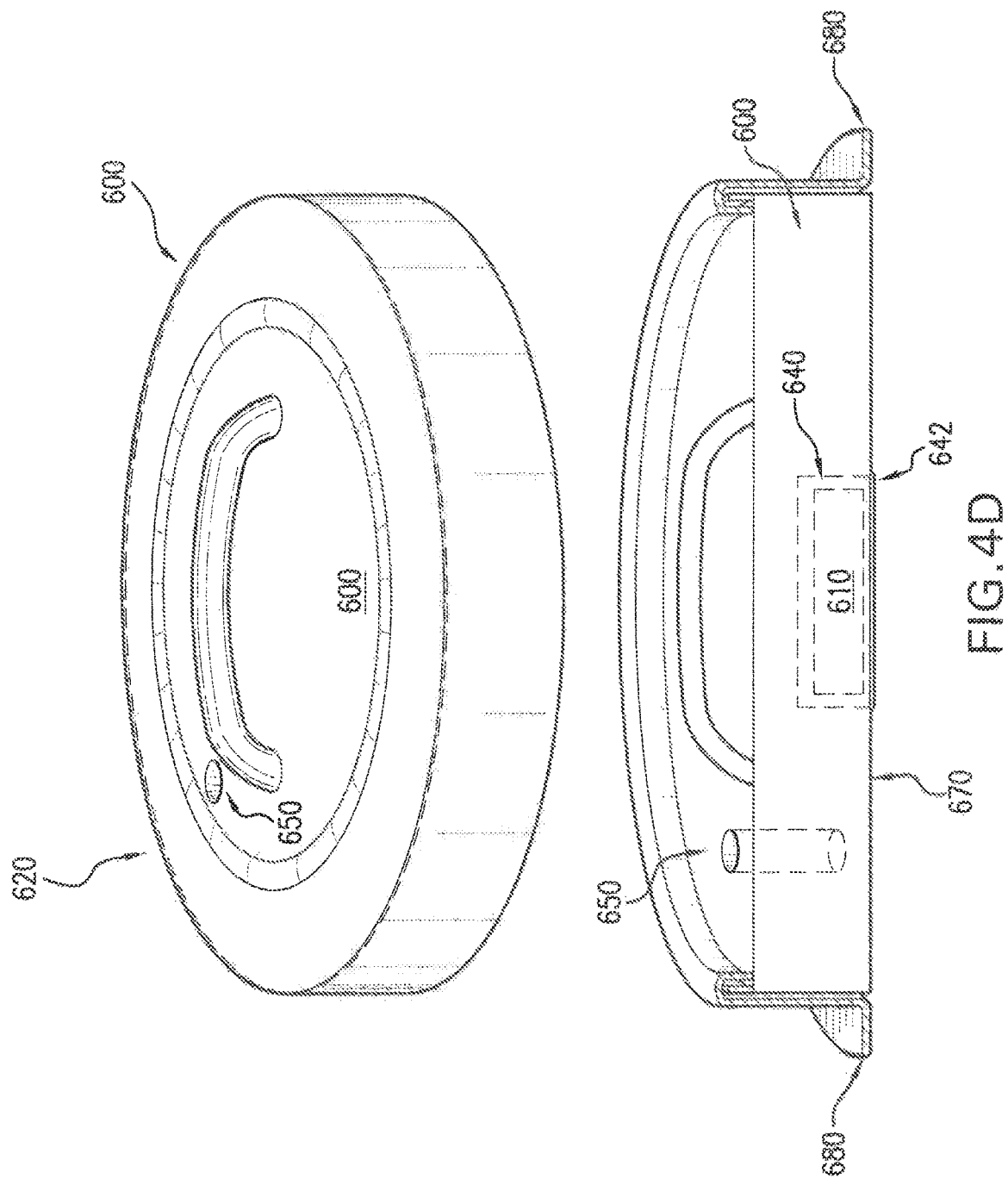
FIG. 4D is an alternative embodiment of an adhesively anchored extracorporeal apparatus.

The extracorporeal apparatus may also be anchored to the patient's body by use of a medical adhesive. A semi-permanent adhesive may be either placed directly on the bottom surface 670 of the extracorporeal apparatus 2, or alternatively, the adhesive may be placed around the edge of the extracorporeal apparatus as shown in FIG. 4D. The rim may be moveable to align with the lower surface 670 of the extracorporeal apparatus 2 when adhering to the patient's body, or retracted above the lower surface 670 of the extracorporeal apparatus when not adhering to the patient's body.

In a standard laparoscopy for endometriosis, three ports are opened on the patient's abdomen—the camera is placed through an umbilical port and two lower quadrant ports are used for instrumentation. Often, there is endometriosis deep in the pelvis or behind the ovary. In order to access the endometriosis and excise or fulgurate it, the surgeon must retract the ovary through one port. The peritoneum must be tented up before the endometriosis can be excised or fulgurated in order to prevent damaging the underlying structures.

With the present invention, the surgeon may start by placing the three ports: a camera in the umbilical port, and two operative ports in the lower quadrants. The surgeon then may engage a clamp intracorporeal apparatus to a placement apparatus. Using one of the operative ports, the surgeon may feed the combination through the trocar into the patient's body, and place the clamp on the ovary to be retracted. The surgeon then is able to place an extracorporeal apparatus on the exterior surface of the abdomen. The magnetic field attracts the clamp and the surgeon is able to guide the ovary towards the extracorporeal apparatus. The extracorporeal apparatus may be locked into position using an adhesive on the extracorporeal apparatus rim or an anchor. With the ovary now retracted against the abdominal wall and maintained by the extracorporeal apparatus, the surgeon is able to disengage the clamp intracorporeal apparatus from the placement apparatus and retract the placement apparatus back through the trocar and out of the patient's body. The ovary will now remain retracted against the interior surface of the anterior abdominal wall, well outside of the surgical field, and without the inclusion of a large intra-abdominal instrument. Accordingly, the surgeon will only need two intra-abdominal instruments, and may control all of the instruments in the operative field without assistance. This also beneficially results in less instrument clutter in the operative field.

The present invention can also be very beneficial when performing a laparoscopic hysterectomy. In an open abdominal hysterectomy, a cork screw is often placed in the fundus of the uterus and used for upward traction in order to decrease bleeding. The traction on the uterus also makes it much easier to access the lateral sides of the uterus and suture and ligate the uterine arteries and cardinal ligaments. One of the difficulties in performing a laparoscopic hysterectomy is that there is no way to retract the uterus in a similar fashion. It is often difficult to surgically place an extra port and use a grasper to retract the uterus. The additional grasper often gets in the way of the other intra-abdominal instruments, which are being used to carry out the dissection. Also, the surgeon is physically unable to manipulate more than two instruments at a time. Lastly, a surgeon often experiences difficulty in trying to manipulate the uterus utilizing a grasper.

The present invention, allows the surgeon the ability to retract the uterus in the same fashion as if the surgeon were performing an open abdominal hysterectomy. Initially, the surgeon would engage a screw intracorporeal apparatus with a placement apparatus, and insert the combination through a trocar into the patient's body. The surgeon is then able to position the screw and twist it into the fundus of the uterus. An extracorporeal apparatus may then be placed on the external anterior abdominal wall. The surgeon must choose an extracorporeal apparatus with a magnet strong enough to attract the muscular and massive uterus. The screw intracorporeal apparatus and the attached uterus would then be attracted towards the magnetic field of the extracorporeal apparatus. Accordingly, the extracorporeal apparatus would essentially provide upwards traction on the uterus similar to an open abdominal case. Furthermore, the extracorporeal apparatus could be moved laterally as needed to move the uterus and allow for easy access to the lateral aspects of the uterus and cervix. With the screw intracorporeal apparatus attached to the uterus, the surgeon may disengage and retract the placement apparatus through the trocar and out of the patient's body, thus freeing space within the body for other intra-abdominal instruments.

The present invention can also be used to increase performance when conducting a salpingectomy for a tubal ligation or an ectopic pregnancy. The current procedure is conducted with use of three ports: an umbilical port for a camera, and two within which to operate. The procedure requires a surgical assistant to grasp and hold the tube while the surgeon performs the resection. However the present invention allows the surgeon to perform the procedure without any assistance, and utilizing only two ports: an umbilical port for the camera, and a superpubic operative port. Initially, the surgeon would begin by engaging a clamp intracorporeal apparatus to a placement apparatus, and passing the combination through a trocar into the patient's body. At this point, the surgeon can maneuver the clamp onto the area of the tube that is to be resected. An extracorporeal apparatus placed on the external abdominal wall could then be used to retract and grasp the tube. With the tube retracted, the surgeon may disengage the placement apparatus and retract it through the trocar and out of the patient's body, thereby freeing up space for a different intra-abdominal apparatus. Next, a harmonic scalpel or other such device would be used to resect the desired portion of the tube. Accordingly, the need for an extra port and a surgical assistant is eliminated. Post-completion of the resection, the surgeon may then reinsert the placement apparatus through the trocar into the patient's body, and manipulate the clamp intracorporeal apparatus still attached to the tube. The surgeon is able to then re-engage the placement apparatus with the intracorporeal apparatus, and release the clamp from the tube. Finally, the surgeon may remove the resected tube from the abdominal cavity, retract the combination of the placement apparatus and the clamp through the trocar and seal the ports used in the surgical procedure.

The present invention may also be used to help the surgeon avoid many of the common complications of laparoscopic surgery. A common complication in laparoscopic surgery is ureteral damage. Ureteral damage, if not promptly treated, may result in damage to renal function and possibly loss of the kidney entirely. The present invention prevents damage to a ureter by the insertion of an intracorporeal apparatus such as a toothless clamp or a loop to move a ureter away from the surgical field.

The present invention may also be used in general surgical procedures. For example, laparoscopic bariatric surgery can be made more efficient using this invention. During a laparoscopic bariatric procedure, the surgeon must retract the liver. Presently, this retractor requires the use of an operative port. The present invention allows the surgeon the ability to retract the liver without the use of a trocar-occupying instrument. Accordingly, the surgery could be performed with a reduced number of ports and reduced intra-abdominal congestion.

The present invention may also be used in laparoscopic procedures performed on animals. For example, laparoscopic surgery routinely performed on baboons may be carried out more efficiently by means of the present invention. During diagnostic laparoscopic procedures, it has been discovered that the uterus and ovaries of a baboon are more mobile than those of humans. The present invention enables the surgeon to retract the uterus or ovaries of a baboon without the use of grasping forceps. This is preferable, because the use of grasping forceps has been reported to result in slight round ligament bleeding in some laparoscopic procedures performed on baboons. Laparoscopic surgery is also performed on other animals, including mammals such as dogs, llamas, alpacas, mares, lions and cows. The present invention will enable surgeons to accomplish such operations in a more efficient manner, as in humans.

Numerous additional advantages may be realized by those having ordinary skill in the art, for any situation in which a surgeon has thorough knowledge of regional anatomy and requires moving internal objects or organs so as to gain access to another object or organ in the body.

What is claimed is:

1. A system for manipulating tissue, comprising:
   an intracorporeal apparatus comprising:
      a main body comprising:
         a first jaw and a second jaw, wherein the first and second jaws are configured to open and close; and
         a node;
   a placement apparatus comprising:
      a body comprising a proximal end comprising a handle comprising a trigger, and a distal end comprising a magnet configured to selectively disengage the intracorporeal apparatus; and
      an actuator disposed within the body,
   wherein the intracorporeal apparatus is releasably coupled to the distal end of the placement apparatus,
   wherein the actuator is configured to apply a force to the node to move one of or both of the first and second jaws,
   wherein movement of the magnet towards the proximal end of the placement apparatus disconnects the intracorporeal apparatus from the distal end of the placement apparatus, and
   wherein movement of the trigger is configured to move at least one of the first and second jaws of the intracorporeal apparatus.

2. The system of claim 1, wherein the intracorporeal apparatus comprises magnetically responsive material.

3. The system of claim 1, wherein movement of the actuator towards the proximal end of the placement apparatus is configured to move the magnet towards the proximal end of the placement apparatus.

4. The system of claim 1, wherein movement of the trigger is configured to disconnect the intracorporeal apparatus from the placement apparatus.

5. A system for manipulating tissue, comprising:
   an intracorporeal apparatus comprising:
      a main body comprising:
         a first jaw and a second jaw, wherein the first and second jaws are configured to open and close;
         a first resealable chamber configured to receive a first removable permanent magnet; and
      a placement apparatus comprising a selective disengagement mechanism configured to selectively disengage the placement apparatus from the intracorporeal apparatus.

6. The system of claim 5, comprising an extracorporeal apparatus comprising a second resealable chamber configured to receive a second removable permanent magnet.

* * * * *